(12) United States Patent
Ouyang et al.

(10) Patent No.: US 8,846,411 B2
(45) Date of Patent: Sep. 30, 2014

(54) DERIVATIVES, REAGENTS, AND IMMUNOASSAY FOR DETECTING LEVETIRACETAM

(75) Inventors: Anlong Ouyang, Fremont, CA (US); Aniruddha Patwardhan, Fishers, IN (US); Lili Arabshahi, Fremont, CA (US)

(73) Assignee: Microgenics Corporation, Fremont, CA (US)

(*) Notice: Subject to any disclaimer, the term of this patent is extended or adjusted under 35 U.S.C. 154(b) by 0 days.

(21) Appl. No.: 12/797,348

(22) Filed: Jun. 9, 2010

(65) Prior Publication Data

US 2010/0317024 A1 Dec. 16, 2010

Related U.S. Application Data

(60) Provisional application No. 61/268,339, filed on Jun. 11, 2009.

(51) Int. Cl.
| | |
|---|---|
| *G01N 33/53* | (2006.01) |
| *C07D 207/09* | (2006.01) |
| *C07K 2/00* | (2006.01) |
| *C07K 16/44* | (2006.01) |
| *G01N 33/94* | (2006.01) |
| *C07D 207/16* | (2006.01) |
| *C07D 207/27* | (2006.01) |
| *C07D 403/12* | (2006.01) |

(52) U.S. Cl.
CPC ............ *C07K 16/44* (2013.01); *G01N 33/9473* (2013.01); *C07D 207/16* (2013.01); *C07D 207/27* (2013.01); *C07D 403/12* (2013.01)
USPC ............ 436/501; 435/7.1; 435/7.9; 548/400; 548/537; 548/550

(58) Field of Classification Search
None
See application file for complete search history.

(56) References Cited

U.S. PATENT DOCUMENTS

| | | |
|---|---|---|
| 7,358,276 B2 | 4/2008 | Differding |
| 2004/0204388 A1 | 10/2004 | Lynch et al. |
| 2008/0009018 A1 | 1/2008 | Ouyang et al. |
| 2008/0199887 A1 | 8/2008 | Valdez |
| 2010/0173427 A1 | 7/2010 | Valdez et al. |

FOREIGN PATENT DOCUMENTS

WO   WO2010048423   4/2010

OTHER PUBLICATIONS

International Search Report and Written Opinion from PCT/US2010/038185, dated Aug. 3, 2010.
Supplemental European Search Report for EP 10801094.3 Dated Nov. 14, 2012.
International Search Report for PCT/US2009/061708 Dated Dec. 22, 2009.
Contin et al., "Levetriacetam Therapeutic Monitoring in Patients with Epilepsy." *Ther Drug Monit.*, vol. 26, No. 4, Aug. 4, 2004.

*Primary Examiner* — Galina Yakovleva
(74) *Attorney, Agent, or Firm* — Workman Nydegger

(57) ABSTRACT

Levetiracetam (LEV) derivatives, methods for synthesizing LEV derivatives, and immunodiagnostic assays for LEV. The synthesis methods described herein include chirally-selective, liquid-phase synthesis steps to produce selected LEV derivatives in high-yield. LEV derivatives can include operative groups, such as: immunogenic moieties that can be used to prepare anti-LEV antibodies; antigenic moieties that can be used in immunodiagnostic assays for LEV; or tracer moieties that can be used in immunodiagnostic assays. Additionally, the LEV derivatives can be used in immunodiagnostic assays to compete with LEV for anti-LEV antibodies.

4 Claims, No Drawings

DERIVATIVES, REAGENTS, AND IMMUNOASSAY FOR DETECTING LEVETIRACETAM

CROSS-REFERENCE TO RELATED APPLICATIONS

This application claims the benefit of and priority to U.S. Provisional Patent Application Ser. No. 61/268,339 filed 11 Jun. 2009 entitled "DERIVATIVES, REAGENTS, AND IMMUNOASSAY FOR DETECTING LEVETIRACETAM" to Ouyang et al., the entirety of which is incorporated herein by reference.

BACKGROUND

Levetiracetam (LEV) ((−)-(S)-α-ethyl-2-oxo-1-pyrrolidine acetamide, Keppra®) was approved by FDA in 2006 as the first-in-class anti-epileptic drug (AED). The compound is marketed under the trade name Keppra® by UCB Pharmaceuticals, Inc.

Levetiracetam is indicated as adjunctive therapy in the treatment of partial onset seizures in adults and children 4 years of age and older, myoclonic seizures in adults and adolescents 12 years of age and older, and primary generalized tonic-clonic seizures in adults and children 6 years of age and older. LEV acts by modulating synaptic neurotransmitter release by binding to the synaptic vesicle protein SV2A in the brain (1). The nominal therapeutic range for LEV is 6-20 ug/mL (2). Therapeutic drug monitoring (TDM) of LEV is important in order to establish an individual's optimum LEV level (3) and to detect non-compliance.

An optimal trough serum/plasma concentration range for LEV is 10-60 mg/L (4-6) LEV is predominantly eliminated via the kidney with approximately 64% of a given dose excreted unchanged in urine. The drug undergoes minimal hepatic metabolism, but hydrolysis of the acetamide function by a cytosolic amidase occurs to produce a carboxylic acid metabolite, 2-pyrrolidone-N-butyric acid. The acid metabolite is excreted in urine and accounts for approximately 27% of the administered dose. Oxidation of the 3 and 4 positions of the 2-oxopyrrolidine ring also occurs by hepatic metabolism to form minor metabolites that account for about 3% of the dose. In addition, LEV and 2-pyrrolidone-N-butyric acid may be oxidized at the 5 position of the 2-oxopyrrolidine ring and then hydrolyzed, resulting in opening of the ring. There is pronounced inter-individual variability in LEV pharmacokinetics. Therefore, therapeutic monitoring of serum/plasma concentration of LEV is recommended.

To date, liquid or gas chromatographic techniques have been employed to measure circulating levels of LEV. However, such methods are impractical for regular TDM due to factors including long sample preparation time, long assay time, high cost, low throughput and labor-intensive procedures. Thus, a fast economical analytical method for measurement of plasma levels of LEV is needed for effective TDM.

Immunoassays are generally regarded as fast, inexpensive and sensitive means for quantifying levels of an antigen present in a sample. Immunoassay techniques have been developed to detect various drugs in biological samples and are well suited for such commercial analytical applications. Accordingly, immunoassays can be used to quickly determine the amount of a drug and/or drug metabolite in a patient's blood, serum, urine, saliva or other body fluids. Examples of immunoassays can include, but not limited to, homogeneous microparticle immunoassay (e.g., immunoturbidimetric) or quantitative microsphere systems ("QMS®"), fluorescence polarization immunoassay ("FPIA"), cloned enzyme donor immunoassay ("CEDIA"), chemiluminescent microparticle immunoassay ("CMIA"), and the like. It would be advantageous to have immunoassays configured to detect LEV in a patient's blood, serum, plasma, and/or other biological fluids or samples. Additionally, it would be advantageous to have LEV derivatives for use in such immunoassays, and/or LEV-based immunogens for use in producing anti-levetiracetam antibodies.

Because at least one antibody specific to the target antigen typically forms the basis of a useful immunoassay, TDM presents a challenge in that most therapeutic drugs are not, by nature, immunogenic and, therefore, do not elicit an immune response when injected into animals commonly used for antibody production such as mice, rabbits, goats, horses and other mammals. Also, active forms of the target drug may be detrimental to the recipient animal, even in small doses. Therefore, a derivative of the therapeutic drug must be made to serve as an immunogen. However, the antibodies produced in response to the immunogen must be able to cross-react with the drug expected to be present in patient samples and, even more preferably, the antibodies should have little, if any, measurable cross-reactivity with inactive metabolic derivatives of the drug that may also be present in the samples.

Immunoassays typically employ other types of derivatives in addition to the immunogen needed for antibody production. By way of non-limiting example, labeled derivatives of a target antigen may be used to compete with the target antigen for binding sites on an antibody capable of recognizing both the target antigen and the labeled derivative. Competitive immunoassays are well known in the current art. Other derivatives may serve as controls or as standards for calibrating the immunoassay.

Levetiracetam, its metabolites, and structurally similar drugs are shown below:

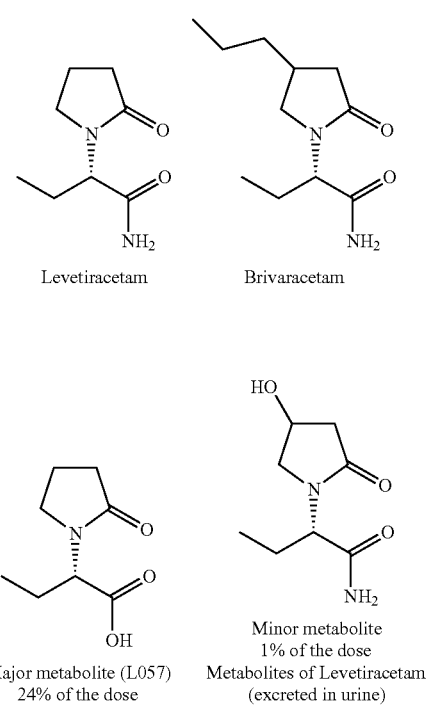

Levetiracetam

Brivaracetam

Major metabolite (L057)
24% of the dose

Minor metabolite
1% of the dose

Metabolites of Levetiracetam (excreted in urine)

-continued

Minor metabolite
2% of the dose

Kenda et al., in attempting to identify derivatives with a higher binding affinity for levetiracetam binding sites than LEV, describe derivatives of LEV including 5-amino-2-(2-oxopyrrolidin-1-yl)pentanoic acid amide (referred to as "analog 56" by Kenda et al.) produced via solid phase synthesis by reductive amination of aldehydic esters. As described, the reaction used 100 grams of rink amide resin and 66 mg of 4-oxobutyric acid 4-methoxybenzyl ester to yield only 2 mg of analog 56 with a purity of 65% as measured by HPLC for a reactive yield of about 0.1%.

Rink amide resin

56

While analog 56 may have promise as a derivative of LEV for use in immunoassays, in order to induce antibody production in a number of animals and monitor antibody production, binding properties and other characteristics, amounts significantly in excess of 2 mg of the immunogenic derivative are required. Likewise, commercialization of an immunoassay comprising a derivative used as a control or standard, or a labeled derivative to compete with target antigen, requires sufficient quantities of the derivative(s) to satisfy commercial demand. So, while the solid phase synthesis method taught by Kenda et al. may be suitable for drug discovery purposes, it has no practical value for producing derivatives for the purpose of developing an immunoassay for LEV.

BRIEF SUMMARY

Generally, the present disclosure relates to levetiracetam (LEV) derivatives, methods for synthesizing LEV derivatives, and immunodiagnostic assays for LEV. LEV derivatives can include operative groups, such as: immunogenic moieties that can be used to prepare anti-LEV antibodies; antigenic moieties that can be used in immunodiagnostic assays for LEV; or tracer moieties that can be used in immunodiagnostic assays. Additionally, the LEV derivatives can be used in immunodiagnostic assays to compete with LEV for anti-LEV antibodies. The synthesis methods described herein include chirally-selective, liquid-phase synthesis steps that are suitable for producing the large amounts of LEV derivatives needed for a successful immunization program for development of antibodies capable of binding LEV and the LEV derivatives with sufficient specificity and sensitivity.

In one embodiment, a chemical composition that includes a LEV derivative of Formula 1 or Formula 2 is disclosed.

Formula 1

Formula 2 n of Formula 2 and L, X, and Y of Formulas 1 and 2 are defined as follows:
a) n is an integer with a value of 0 to 8;
b) L is one of the group consisting of $CH_2$, CO, NHCO, NHCOO, CONH, NH, O, or S, and combinations thereof;
c) X is an end group, an aromatic group, an aryl group, or a saturated, unsaturated, substituted, unsubstituted, straight chain, or branched chain aliphatic group having from 1 to 10 carbon and/or hetero chain atoms, the hetero chain atoms being selected from the group consisting of oxygen, nitrogen, sulfur, or phosphorus, and combinations thereof; and
d) Y is optional and if present is one of a functional group selected from group consisting of alcohol amine, amide, carboxylic acid, aldehyde, ester, iminoester, isocyanate, isothiocyanate, anhydride, thiol, thiolacetone, diazonium, N-hydroxysuccinimide ("NHS"), CO—NHS, O—NHS, maleimido; or
e) Y is a $Y_1$ —Z where $Y_1$ is selected from the group consisting of COO, CO, O, CONH, NHCO, or NH and Z is an operative group.

The definition of Formula 2 presented herein includes a number of possible compounds. However, 5-Amino-2-(2-oxopyrrolidin-1-yl)pentanoic Acid Amide (Formula 3), which is shown below, is specifically excluded from the class of compounds of Formula 2 claimed herein.

Formula 3

In one embodiment of the method, the operative group of Z is selected from the group consisting of detectable labels, antigenic carriers, coupling agents, end groups, proteins, lipoproteins, glycoproteins, polypeptides, polysaccharides, nucleic acids, polynucleotides, teichoic acids, radioactive isotopes, enzymes, enzyme fragments, enzyme donor fragments, enzyme acceptor fragments, enzyme substrates, enzyme inhibitors, coenzymes, fluorescent moieties, phosphorescent moieties, anti-stokes up-regulating moieties, chemiluminescent moieties, luminescent moieties, dyes, sensitizers, particles, microparticles, magnetic particles, solid supports, liposomes, ligands, receptors, hapten radioactive isotopes, and combinations thereof.

In a specific example a chemical composition that includes a LEV derivative of Formula 1 or Formula 2, n is an integer with a value of 0, 1, 2, 3, or 4, L is one of the group consisting of NHCOO, NH, NHCO, $CH_2$, CO, S, or CONH, X is one of the group consisting of H, phenyl ("Ph"), $OCH_2$—Ph, NH, O, O—NHS, $CH_2$, H, Maleimido-Ph, $CH_2$—$CH_2$—NH, and Y is optional and if present is H or Y is optional and if present is a $Y_1$—Z where $Y_1$ CO and Z is one of the group consisting of —NHS, —BSA, or —KLH.

In a specific example, n, L, X, and Y or $Y_1$—Z of Formula 2 are selected from the group consisting of:
  a) n=4, L=NHCOO, and X=t-butyl;
  b) n=4, L=NH, and X=H;
  c) n=4, L=NHCO, and X=$OCH_2$-Ph
  d) n=4, L=NHCO, X=Ph, and $Y_1$—Z=CO—NHS;
  e) n=4, L=NHCO, X=Ph, and $Y_1$—Z=CO—KLH;
  f) n=4, L=NHCO, X=Ph, and $Y_1$—Z=CO—BSA;
  g) n=3, L=$CH_2$, X=NH, and $Y_1$—Z=CO—BSA;
  h) n=2, L=CO, and X=$OCH_2$-Ph;
  i) n=2, L=CO, X=O, and Y=H;
  j) n=2, L=CO, and X=O—NHS;
  k) n=0, L=$CH_2$, X=$CH_2$, and $Y_1$—Z=CO—KLH;
  l) n=0, L=$CH_2$, X=$CH_2$, and $Y_1$13 Z=CO—BSA;
  m) n=1, L=S, and X=$CH_2$-Ph;
  n) n=1, L=S, and X=H;
  o) n=1, L=S, X=Maleimido-Ph, and $Y_1$—Z=CO—BSA; or
  p) n=1, L=S, X=Maleimido-Ph, and $Y_1$—Z=CO—KLH.

In another specific example, L, X, Y, and $Y_1$—Z of Formula 1 are selected from the group consisting of:
  a) L=CONH, X=$CH_2$—$CH_2$—NH, and Y=H,
  b) L=CONH, X=$CH_2$—$CH_2$—NH, and $Y_1$—Z=CO—KLH; or
  c) L=CONH, X=$CH_2$—$CH_2$—NH, and $Y_1$—Z=CO—BSA.

In another embodiment, a kit for use in an immunodiagnostic assay for detecting the presence of LEV in a sample is disclosed. The kit includes a LEV derivative having a chemical structure of one of Formula 1 or Formula 2;

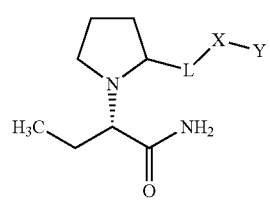

Formula 1

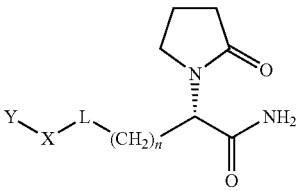

Formula 2 and an anti-LEV antibody having at least one binding domain, the antibody having a portion capable of binding LEV and/or a LEV derivative, wherein an interaction between the antibody and the LEV derivative is at least 50% of at least one of affinity, specificity, or avidity of the antibody for LEV. The definitions of n, L, X, and Y are the same as defined above with respect to the chemical composition.

In one embodiment, the LEV derivative or anti-LEV antibody is coupled with one of a particle, magnetic particle, microparticle, microsphere, support, enzyme donor, or enzyme acceptor.

In one embodiment, the kit further includes at least one of the following:
  a) a stock composition of LEV;
  b) a series of compositions containing LEV at different concentrations, the series of compositions forming a concentration gradient;
  c) the LEV derivative having a tracer conjugate;
  d) the LEV derivative coupled to a microparticle;
  e) the antibody coupled to a microparticle;
  f) the LEV derivative having an enzyme donor, and a corresponding enzyme acceptor;
  g) the LEV derivative having an enzyme acceptor, and a corresponding enzyme donor; or
  h) the antibody loaded on a particle suitable for separation by filtration or sedimentation.

In yet another embodiment, an antibody composition for use in an immunodiagnostic system for detecting the presence of LEV in a sample is disclosed. The antibody composition includes an anti-LEV antibody produced by an immunogenic composition that includes a LEV derivative, the LEV derivative having a chemical structure of Formula 1 or Formula 2

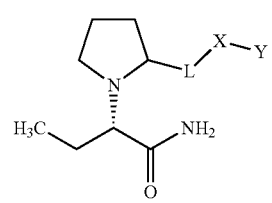

Formula 1

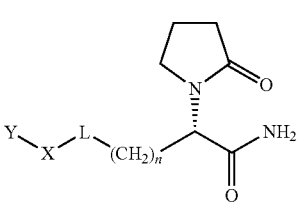

Formula 2 wherein
  a) n is an integer with a value of 0 to 8;
  b) L is one of the group consisting of $CH_2$, CO, NHCO, NHCOO, CONH, NH, O, or S, and combinations thereof;

c) X is an end group, an aromatic group, an aryl group, or a saturated, unsaturated, substituted, unsubstituted, straight chain, or branched chain aliphatic group having from 1 to 10 carbon and/or hetero chain atoms, the hetero chain atoms being selected from the group consisting of oxygen, nitrogen, sulfur, or phosphorus, and combinations thereof; and d) Y is a $Y_1$—Z where $Y_1$ is selected from the group consisting of COO, CO, O, CONH, NHCO, or NH and Z is an operative group.

In one embodiment, at least one of the affinity, the specificity, or the avidity of the antibody for the LEV derivative compared to LEV is sufficient for use in a homogeneous or heterogeneous immunodiagnostic assay. In one embodiment, an interaction between the antibody and the LEV derivative is at least 50%, at least 70%, or at least 90% of at least one of affinity, specificity, or avidity of the antibody for LEV.

In one embodiment, the immunogenic moiety is selected from the group consisting of proteins, polypeptides, glycoproteins, polysaccharides, particles, microparticles, nucleic acids, polynucleotides, and combinations thereof. In another embodiment, the immunogenic moiety is a protein selected from the group consisting of bovine serum albumin ("BSA"), keyhole limpet hemocyanin ("KLH"), egg ovalbumin, bovine gamma-globulin ("BGG"), and combinations thereof.

In one embodiment, the antibody is a monoclonal antibody. In another embodiment, the antibody is a polyclonal antibody.

An anti-LEV antibody can be produced according to a method that includes a) administering at least a first dose of an immunogenic composition that includes a LEV derivative to an antibody producing subject, the LEV derivative having a chemical structure of Formula 1 or Formula 2

Formula 1

Formula 2 b) collecting the antibodies from the antibody producing subject; and c) purifying and/or screening the antibodies collected from the antibody producing subject.

In one embodiment, the method for producing an anti-LEV antibody further includes administering to the antibody producing subject at least a second dose of the immunogenic composition prior to collecting the antibody from the antibody producing subject.

In one embodiment, the collecting includes at least one of obtaining blood, serum, plasma, or other biological sample from the antibody producing subject.

In one embodiment, the screening includes and ELISA assay.

In still yet another embodiment, the present invention includes a liquid phase synthesis method for synthesizing a levetiracetam ("LEV") derivative of Formula 1 or Formula 2.

Formula 1

Formula 2

The method includes (1) providing a protected amino acid starting material, and (2) modifying the protected amino acid starting material to yield a LEV derivative of Formula 1 or Formula 2. n of Formula 2 and L, X, and Y of Formulas 1 and 2 are defined as follows:

a) n is an integer with a value of 0 to 8;

b) L is one of the group consisting of $CH_2$, CO, NHCO, NHCOO, CONH, NH, or S, and combinations thereof;

c) X is an end group, an aromatic group, an aryl group, or a saturated, unsaturated, substituted, unsubstituted, straight chain, or branched chain aliphatic group having from 1 to 10 carbon and/or hetero chain atoms, the hetero chain atoms being selected from the group consisting of oxygen, nitrogen, sulfur, or phosphorus, and combinations thereof; and d) Y is optional and if present is one of a functional group selected from group consisting of alcohol amine, amide, carboxylic acid, aldehyde, ester, iminoester, isocyanate, isothiocyanate, anhydride, thiol, thiolacetone, diazonium, NHS, CO—NHS, O—NHS, maleimido; or e) Y is optional and if present is a $Y_1$—Z where $Y_1$ is selected from the group consisting of COO, CO, O, CONH, NHCO, or NH and Z is an operative group.

Suitable examples of protected amino acid starting materials may include protected derivatives of natural and unnatural amino acids that have a derivatizable functional group on the side chain. Illustrative examples of naturally occurring amino acids having a side chain functional group that can be derivatized to make LEV derivatives in the methods described herein include, but are not limited to, protected derivatives of arginine, histidine, lysine, aspartic acid, glutamic acid, serine, threonine, asparagine, glutamine, cysteine, phenylalanine, tryptophan, and tyrosine. In one embodiment, the protected amino acid derivative includes a traceable moiety such as, but not limited to, a fluorescent moiety that can be used to monitor the starting materials, intermediates, and products.

Specific examples of protected amino acid starting materials include H-Lys(Boc)-$NH_2$, H-Lys(Boc)-OMe, H-lys(Z)-OtBu, H-Glu(OBzl)-OtBu, H-Cys(Bzl)-OMe, FMOC-Pro-OH, and Boc-Pro-OH. Preferably the protected amino acid starting material for the synthesis of compounds of Formula 2 is selected from the group consisting of H-lys(Z)-OtBu, H-Glu(OBzl)-OtBu, and H-Cys(Bzl)-OMe. Preferably the protected amino acid starting material for the synthesis of compounds of Formula 1 is selected from the group consisting of FMOC-Pro-OH and Boc-Pro-OH.

In one embodiment, a synthetic yield for the levetiracetam ("LEV") derivative of Formula 1 or Formula 2 is in a range from about 10% to about 40%. In another embodiment, the synthetic yield for the LEV derivative of Formula 1 or Formula 2 is in a range from about 5% to about 25%. In yet another embodiment, the yield for the LEV derivative of Formula 1 or Formula 2 is in a range from about 1% to about 10%. As used herein, the term "synthetic yield" refers to the yield of product (i.e., product/starting material) in a reaction step or the product of the synthetic yields from each step in a multi-step synthesis. That is, the synthetic yield for a three-step synthesis reaction is defined as follows: synthetic yield=% yield step 1×% yield step 2×% yield step 3. A similar method can be used to calculate the synthetic yield for a synthetic scheme having more or fewer steps.

Because the synthesis reactions described herein are conducted in liquid phase, it is important to be able to track the starting materials, intermediates, and products. As such, the methods described herein further include monitoring a synthesis of at least one of a starting material, a synthesis intermediate, or a LEV derivative of Formula 1 or Formula 2 using a traceable moiety. In one embodiment, the traceable moiety includes a fluorescent moiety.

In still yet another embodiment, the present invention includes a liquid phase synthesis method for synthesizing a levetiracetam ("LEV") derivative of Formula 2.

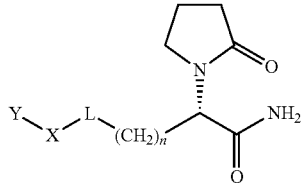

Formula 2

The method includes (1) providing a protected amino acid starting material, and modifying the protected amino acid starting material to yield a LEV derivative of Formula 2. n, L, X, and Y of Formula 2 are defined as follows:
a) n is an integer with a value of 0 to 8;
b) L is one of the group consisting of $CH_2$, CO, NHCO, NHCOO, NH, or S, and combinations thereof;
c) X is an end group, an aromatic group, an aryl group, or a saturated, unsaturated, substituted, unsubstituted, straight chain, or branched chain aliphatic group having from 1 to 10 carbon and/or hetero chain atoms, the hetero chain atoms being selected from the group consisting of oxygen, nitrogen, sulfur, or phosphorus, and combinations thereof; and
d) Y is optional and if present is one of a functional group selected from group consisting of alcohol amine, amide, carboxylic acid, aldehyde, ester, iminoester, isocyanate, isothiocyanate, anhydride, thiol, thiolacetone, diazonium, NHS, CO—NHS, O—NHS, maleimido; or
e) Y is a $Y_1$—Z where $Y_1$ is selected from the group consisting of COO, CO, O, CONH, NHCO, or NH and Z is an operative group.

In one embodiment, the method for synthesizing a compound of Formula 2 further includes (1) providing a single stereoisomer of the protected amino acid starting material, wherein the single stereoisomer of the protected amino acid starting material has a selected stereochemical orientation around at least one stereocenter that includes an amine functional group, (2) adding an alkyl group to the amine functional group on the protected amino acid starting material using an alkylating agent, and (3) cyclizing at least a portion of the alkyl group to produce a single stereoisomer of a LEV derivative, wherein the single stereoisomer of the LEV derivative has a selected stereochemical orientation around at least one covalent bond that is the same as the stereochemical orientation in the protected amino acid starting material.

In one embodiment, the alkylating agent is a 4-substituted butyrate derivative, wherein the derivatizing group is an electron withdrawing/leaving group that renders the butyrate susceptible to nucleophilic attack. Suitable examples of 4-substituted butyrate derivatives include, but are not limited to, halo butyrates such as ethyl 4-fluorobutyrate, ethyl 4-chlorobutyrate, ethyl 4-bromobutyrate, and ethyl 4-iodobutyrate In still yet another embodiment, the present invention includes a method of performing an immunodiagnostic assay for detecting the presence of LEV in a sample obtained from a subject previously administered LEV. The method includes:
a) combining an anti-LEV antibody and a LEV derivative with a sample to form a first composition, said antibody being capable of binding LEV and the LEV derivative, wherein an interaction between the antibody and the LEV derivative is at least 50% of at least one of affinity, specificity, or avidity of the antibody for LEV, and wherein the LEV derivative has a chemical structure of one of Formula 1 or Formula 2;

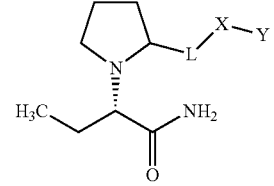

Formula 1

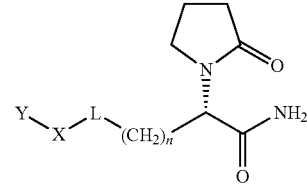

Formula 2 b) allowing any free LEV from the sample and the LEV derivative to compete for binding with the antibody; and
c) detecting binding between the LEV derivative and the antibody.

In one embodiment, the method of performing an immunodiagnostic assay for detecting the presence of LEV in a sample obtained from a subject previously administered LEV further includes:
a) obtaining the LEV derivative, said LEV derivative including a fluorescent moiety;
b) exciting the fluorescent conjugate with polarized light having a first amount of polarization;
c) detecting polarized light emitted from the fluorescent conjugate having a second amount of polarization;
d) comparing the first amount of polarization with the second amount of polarization; and e) determining whether LEV is present in the sample, wherein the second amount of polarization being different from the first amount of polarization is an indication that LEV is present in the sample.

The above method further includes:
a) combining a known amount of LEV with the LEV derivative and antibody to form a control binding composition;
b) detecting polarized light emitted from the florescent conjugate in the control binding composition having a third amount of polarization;
c) comparing the third amount of polarization with the second amount of polarization; and
d) determining the amount of LEV present in the sample.

In another embodiment, the method of performing an immunodiagnostic assay for detecting the presence of LEV in a sample obtained from a subject previously administered LEV further includes:
a) obtaining the LEV derivative and antibody, wherein one of the LEV derivative and antibody is coupled to a microparticle;
b) irradiating the first composition with incident light;
c) detecting a first intensity of light transmitted from the first composition;
d) identifying a minimum intensity of light transmitted from a control binding composition having the LEV derivative and antibody and not having free LEV;
e) comparing the minimum intensity of transmitted light with the first intensity of the transmitted light; and
f) determining whether LEV is present in the sample, wherein the minimum intensity being different from the first intensity is an indication that LEV is present in the sample.

The above method further includes:
a) combining a known amount of LEV with the LEV derivative and antibody to form a control binding composition;
b) irradiating the control binding composition with incident light;
c) detecting a second intensity of light transmitted from the control binding composition; and
d) determining the amount of LEV present in the sample, wherein a comparison between the first intensity and the second intensity is an indication of the amount of LEV present in the sample.

In yet another embodiment, the method of performing an immunodiagnostic assay for detecting the presence of LEV in a sample obtained from a subject previously administered LEV further includes:
a) obtaining the LEV derivative, wherein the LEV derivative includes an enzyme donor;
b) combining an enzyme acceptor with the first composition;
c) combining a substrate with the first composition, wherein the substrate is cleavable by interacting with the enzyme donor and enzyme acceptor; and
d) detecting enzyme activity.

The above method further includes:
a) combining a known amount of LEV with the LEV derivative and antibody to form a control binding composition;
b) combining an enzyme acceptor with the control binding composition;
c) combining a substrate with the control binding composition, wherein the substrate is cleavable by interacting with the enzyme donor and enzyme acceptor;
d) detecting control enzyme activity; and
e) determining the amount of LEV present in the sample, wherein a comparison between the enzyme activity and the control enzyme activity is an indication of the amount of LEV present in the sample.

In still yet another embodiment, the method of performing an immunodiagnostic assay for detecting the presence of LEV in a sample obtained from a subject previously administered LEV further includes:
a) obtaining the LEV derivative, wherein the LEV derivative includes a tracer moiety;
b) separating the antibody from the competitive binding composition;
c) separating unbound LEV derivative from the antibody; and
d) detecting the tracer moiety of the analog bound with the antibody.

The above method further includes:
a) combining a known amount of LEV with the LEV derivative and antibody to form a control binding composition;
b) separating the antibody from the control binding composition;
c) detecting a first amount of tracer conjugate bound with the antibody from the competitive binding composition;
d) detecting a second amount of tracer conjugate bound with the antibody from the control binding composition; and
e) determining the amount of LEV present in the sample, wherein a comparison between the first amount of tracer conjugate and the second amount of tracer conjugate is an indication of the amount of LEV present in the sample.

These and other objects and features of the present invention will become more fully apparent from the following description and appended claims, or may be learned by the practice of the invention as set forth hereinafter.

DETAILED DESCRIPTION

I. Introduction

Generally, the present invention relates to levetiracetam (LEV) derivatives, methods for synthesizing LEV derivatives, and immunodiagnostic assays for LEV. LEV derivatives can include operative groups, such as: immunogenic moieties that can be used to prepare anti-LEV antibodies; antigenic moieties that can be used in immunodiagnostic assays for LEV; or tracer moieties that can be used in immunodiagnostic assays. Additionally, the LEV derivatives can be used in immunodiagnostic assays to compete with LEV for anti-LEV antibodies. The synthesis methods described herein include chirally-selective, liquid-phase synthesis steps that are suitable for producing the large amounts of LEV derivatives needed for a successful immunization program for development of antibodies capable of binding LEV and/or the LEV derivatives with sufficient specificity and sensitivity.

II. Levetiracetam Derivatives

In one embodiment of the invention, LEV derivatives are provided having a structure based upon Formula 1 or Formula 2.

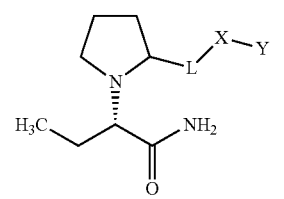

Formula 1

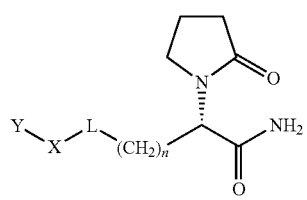

Formula 2

The foregoing chemical structures of Formula 1 and/or Formula 2 are scaffolds that can include a variety of moieties conjugated thereto. As such, the scaffolds can be further defined by the following:

(a) n is an integer with a value of 0 to 8;
(b) L is one of the group consisting of $CH_2$, CO, NHCO, NHCOO, CONH, NH, O, or S, and combinations thereof;
(c) X is an end group (e.g., H), an aromatic group, an aryl group, or a saturated, unsaturated, substituted, unsubstituted, straight chain, or branched chain aliphatic group having from 1 to 10 carbon and/or hetero chain atoms, the hetero chain atoms being selected from the group consisting of oxygen, nitrogen, sulfur, or phosphorus, and combinations thereof; and
(d) Y is optional and if present is one of a functional group selected from group consisting of alcohol amine, amide, carboxylic acid, aldehyde, ester, iminoester, isocyanate, isothiocyanate, anhydride, thiol, thiolacetone, diazonium, NHS, CO—NHS, O—NHS, maleimido; or
(e) Y is a $Y_1$—Z where $Y_1$ is selected from the group consisting of COO, CO, O, CONH, NHCO, or NH and Z is an operative group.

Suitable examples of aromatic and aryl X groups include, but are not limited to, benzene, phenyl, benzyl, toluene, toluoyl, xylene, and the like. The aromatic group can also include hetero atoms so as to be a hetero aromatic such as pyridine, furan, tetrahydrofuran, and the like. Also, an aromatic can be a polycyclic aromatic such as naphthalene, anthracene, phenanthrene, polycyclic aromatic hydrocarbons, indole, quinoline, isoquinoline, and the like. The term "aryl" includes aromatic ring systems with 6 to 14 carbon atoms, the aromatic ring systems including one or more rings having from 6 to 14 ring atoms wherein at least one ring is aromatic. Examples of $C_{6-14}$aryl groups include phenyl ($C_6$), indenyl ($C_9$), naphthyl ($C_{10}$), fluorenyl ($C_{13}$), anthracyl ($C_{14}$), and phenanthryl ($C_{14}$). In the above mentioned aryl groups, unless otherwise stated, one or more hydrogen atoms may optionally be replaced by other substituent groups. For example, aryl groups may be substituted by the following substituents groups: OH; $NO_2$; CN; $NH_2$; halogen, for example fluorine or chlorine; optionally substituted $C_{1-10}$alkyl, for example methyl, ethyl, or propyl; optionally substituted —$OC_{1-3}$alkyl, for example —OMe, —OEt, —COOH, —COO—$C_{1-4}$alkyl, for example —COOMe or —COOEt, or —$CONH_2$.

Suitable examples of aliphatic X groups include, but are not limited to, $CH_2$; $(CH_2)_2$; $(CH_2)_3$; $(CH_2)_4$; $(CH_2)_5$; $(CH_2)_6$; $COCH_2$; $CO(CH_2)_2$; $CO(CH_2)_3$; $CO(CH_2)_4$; $CO(CH_2)_5$; $CO(CH_2)_6$; $CH_2NH$, $(CH_2)_2NH$, $(CH_2)_3NH$, $(CH_2)_4NH$, $(CH_2)_5NH$, $(CH_2)_6NH$, maleimido-Ph, t-butyl, Ph, $OCH_2$-Ph, NH, $CH_2$-Ph, combinations thereof, and the like.

Suitable examples of Z of $Y_1$—Z include, but are not limited to, a detectable label, an antigenic carrier, or an end group selected from the group consisting of proteins, enzymes, enzyme fragments, fluorescent compounds, chemiluminescent materials, electrochemical mediators, particles, reporter groups, enzyme inhibitors, and/or nucleic acids.

In one illustrative example, suitable examples of Z operative groups include, but are not limited to, The method of claim 11, wherein the operative group is selected from the group consisting of detectable labels, antigenic carriers, coupling agents (e.g., NHS, CO—NHS, O—NHS, maleimido, etc), end groups, proteins, lipoproteins, glycoproteins, polypeptides, polysaccharides, nucleic acids, polynucleotides, teichoic acids, radioactive isotopes, enzymes, enzyme fragments, enzyme donor fragments, enzyme acceptor fragments, enzyme substrates, enzyme inhibitors, coenzymes, fluorescent moieties, phosphorescent moieties, anti-stokes up-regulating moieties, chemiluminescent moieties, luminescent moieties, dyes, sensitizers, particles, microparticles, magnetic particles, solid supports, liposomes, ligands, receptors, hapten radioactive isotopes, and combinations thereof. In another illustrative example, Z can be any of the following conjugate groups: (a) BSA; (b) KLH; (c) fluorescent tracer; and (d) the like.

Tables 1 and 2 shown below illustrate a number of specific LEV derivatives and their corresponding L, X, Y, and $Y_1$—Z groups. Synthetic yields for a number of the LEV derivatives are shown as well.

TABLE 1

LEV derivatives of Formula 2

| LEV derivative | n | L | X | Y | $Y_1$—Z | Percent Yield |
|---|---|---|---|---|---|---|
| 2 | 4 | NHCOO | t-butyl | — | — | |
| 3 | 4 | NH | H | — | — | ~5-26% |
| 15 | 4 | NHCO | $OCH_2$-Ph | — | — | ~10-38% |
| 17 | 4 | NHCO | Ph | — | CO-NHS | ~1-10% |
| 18a | 4 | NHCO | Ph | — | CO-KLH | |
| 18b | 4 | NHCO | Ph | — | CO-BSA | |
| 19 | 4 | $CH_2$ | NH | — | CO-BSA | |
| 24 | 2 | CO | $OCH_2$-Ph | — | — | ~7-26% |
| 25 | 2 | CO | O | H | — | ~3.5-18.5% |
| 26 | 2 | CO | O—NHS | — | — | ~2-13% |
| 27 | 0 | $CH_2$ | $CH_2$ | — | CO-KLH | |
| 28 | 0 | $CH_2$ | $CH_2$ | — | CO-BSA | |
| 33 | 1 | S | $CH_2$-Ph | — | — | ~9-26% |
| 34 | 1 | S | H | — | — | ~4.5-19% |
| 37 | 1 | S | Maleimido-Ph | — | CO-KLH | |
| 38 | 1 | S | Maleimido-Ph | — | CO-BSA | |

TABLE 2

LEV derivatives of Formula 1

| LEV derivative | L | X | Y | Y$_1$—Z | Percent Yield |
|---|---|---|---|---|---|
| 43 | CONH | CH$_2$—CH$_2$—NH | H | — | ~8-18% |
| 44 | CONH | CH$_2$—CH$_2$—NH | — | CO-KLH | |
| 45 | CONH | CH$_2$—CH$_2$—NH | — | CO-BSA | |

The structure of each of the LEV derivatives in Tables 1 and 2 is shown in the following sections. In addition, synthesis schemes the LEV derivatives are shown in the following sections and are discussed in detail in the accompanying Examples.

III. LEV Derivatives of Formula 2

Several schemes for synthesizing a derivative based upon Formula 2 were designed. In general, synthesis is facilitated if the starting material is commercially available and if progress of the reaction can be monitored via detection of the reaction products at each step. Detection of reaction products may be performed by any suitable means with preference given to quick methods such as detection via fluorescent moiety, for example, an ultra-violet light sensitive chromophore. For example, reactants and products can be separated by high-performance liquid chromatography (HPLC) or thin layer chromatography (TLC) and the presence of reactants, intermediates, and products can be monitored using a detectable label such as a chromophore attached to one or more of the reactants, intermediates, and products.

Scheme 1 shown below is based on known synthetic procedures and utilizes a commercially available starting material, H-Lys (Boc)-NH2. However, 4-oxobutyric acid is not readily available and, even if it was available, the lack of a detectable moiety, such as a chromophore, on the starting material or product makes monitoring the reaction challenging.

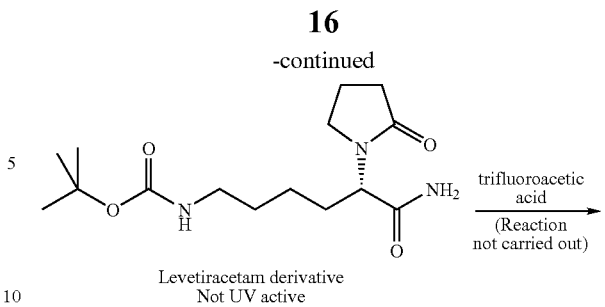

Levetiracetam derivative
Not UV active

2

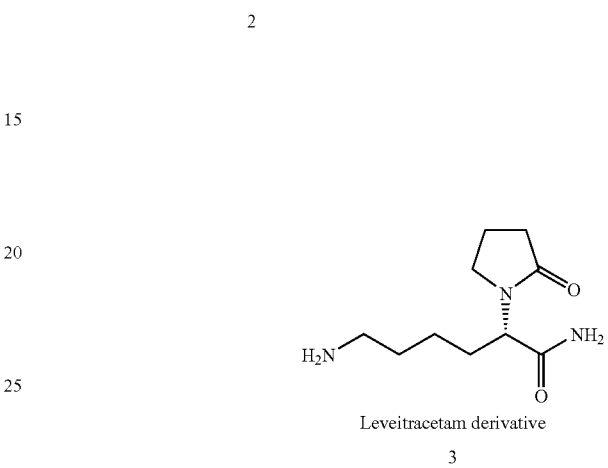

Leveitracetam derivative

3

Schemes 2 and 2' are based on two new synthetic pathways, using the commercially available starting material H-Lys (Boc)-NH2. However, the cyclized product was not isolated because lack of a chromophore on the starting material or product rendered the isolation, purification and characterization difficult. Likewise, analytical techniques such as TLC, HPLC and LC/MS are not useful for monitoring the reaction progress. Staining techniques (iodine, anisaldehyde, phosphoric acid) are not reliable since no reference product is available for comparison. In addition, reactive terminal amide —CO—NH2 could interfere with cyclization reactions.

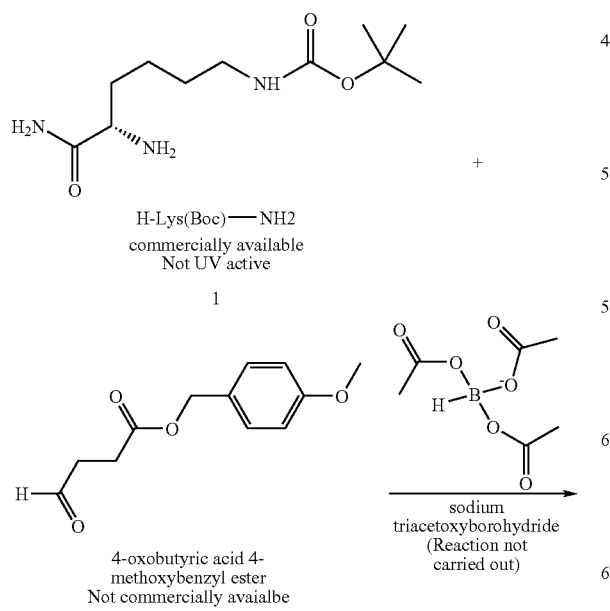

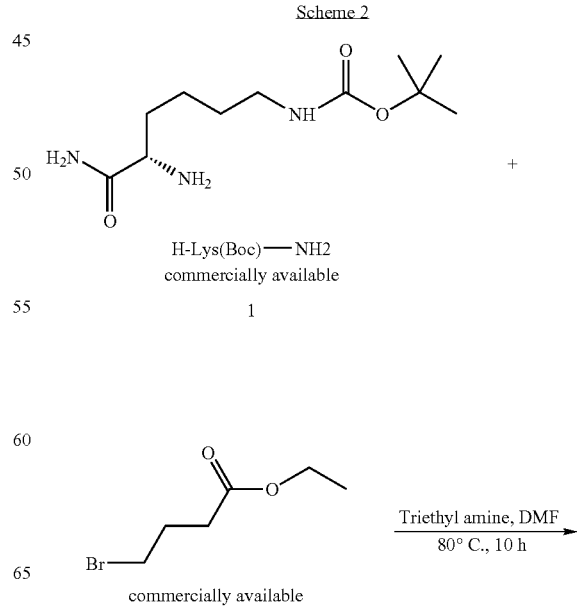

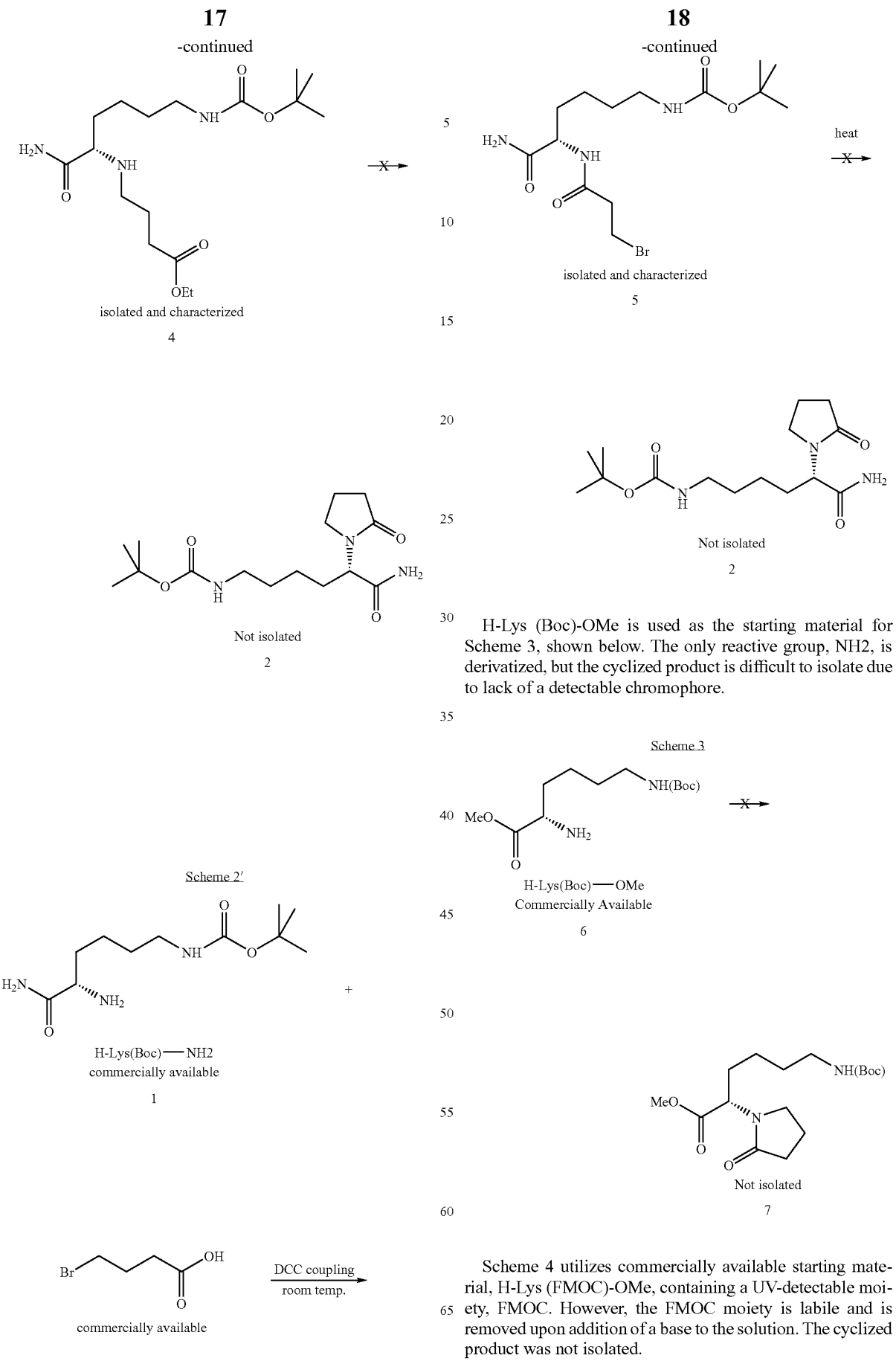

H-Lys (Boc)-OMe is used as the starting material for Scheme 3, shown below. The only reactive group, NH2, is derivatized, but the cyclized product is difficult to isolate due to lack of a detectable chromophore.

Scheme 4 utilizes commercially available starting material, H-Lys (FMOC)-OMe, containing a UV-detectable moiety, FMOC. However, the FMOC moiety is labile and is removed upon addition of a base to the solution. The cyclized product was not isolated.

Scheme 4

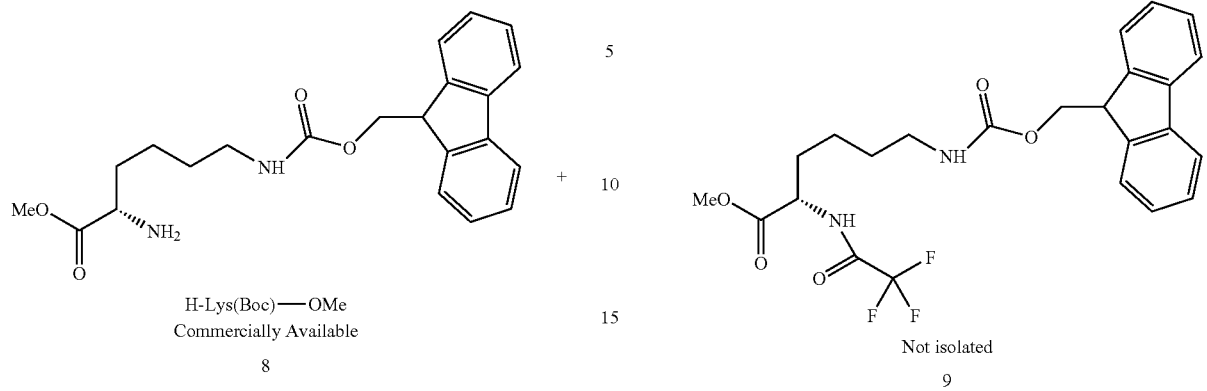

H-Lys(Boc)—OMe
Commercially Available
8

9
Not isolated

Scheme 5 utilizes commercially available starting material, H-Lys (Z)-OtBu, which contains a UV-detectable moiety. Alkylation and cyclization reactions are monitored via TLC or HPLC. Purification and isolation is achieved via column chromatography. Cyclization chemistry is facilitated with the reactive group (alpha amine) and chemically stable protective group (Benzyl).

Scheme 5

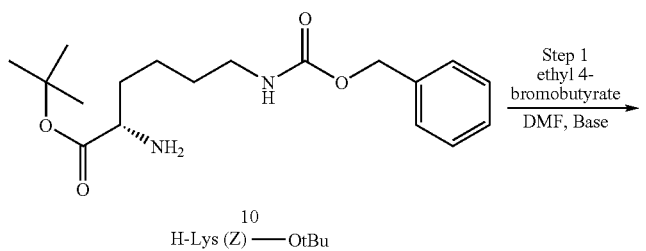

10
H-Lys (Z)—OtBu

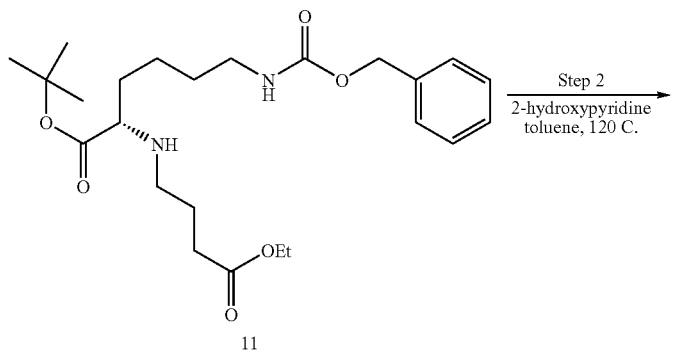

11

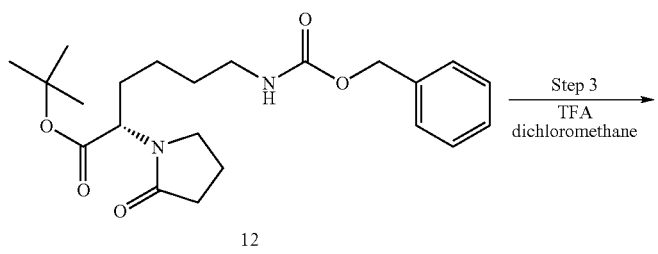

12

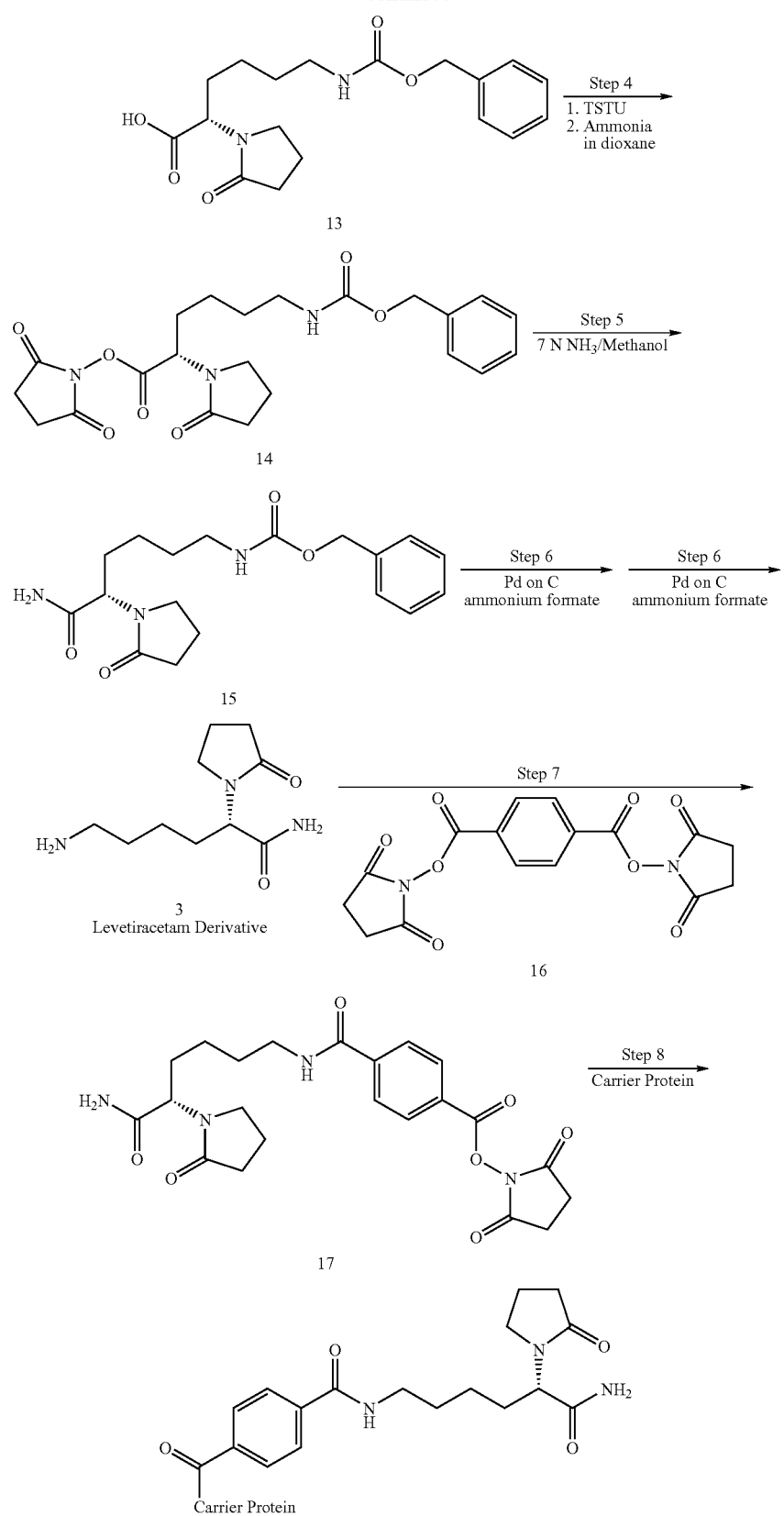

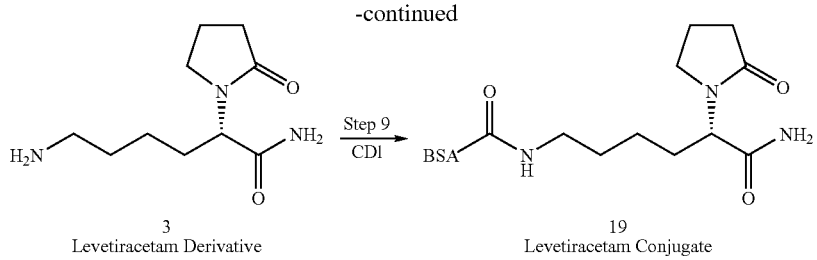

-continued

3
Levetiracetam Derivative

19
Levetiracetam Conjugate

Compound 18a was used as an immunogen to produce a suitable antibody with desirable specificity, sensitivity and cross-reactivity for a commercial LEV immunoassay.

Scheme 6 utilizes commercially available UV-detectable starting material, H-Glu (Obzl)-OtBu. Alkylation and cyclization reactions are monitored via TLC or HPLC. Purification and isolation of the products is carried out via column chromatography. The cyclization chemistry is facilitated with the reactive alpha amine group and chemically stable protective benzyl group. Scheme 6 is a suitable alternative to Scheme 5 for production of LEV derivatives including an immunogenic derivative.

Scheme 6

H-Glu(OBzI) ——OtBu
Bachem (Cat No. E 3535)

21

22

-continued

23

24

25

26

27
Levetiracetam Immunogen
(Formula 2c)

-continued
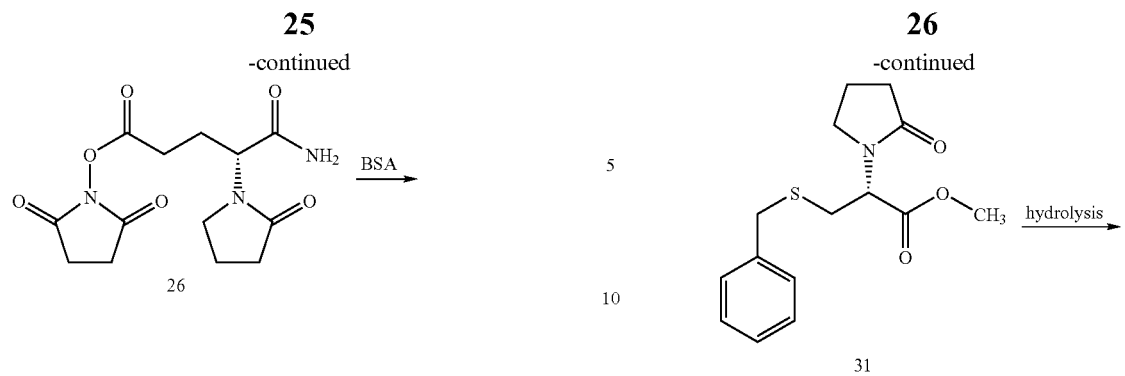
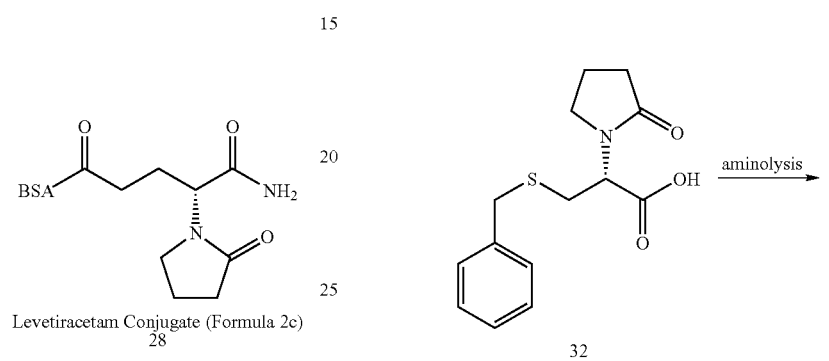
Levetiracetam Conjugate (Formula 2c)
28
Scheme 7 uses a commercially available material, H-Cys(Bzl)-OMe, containing a detectable chromophore. Scheme 7 serves as a useful alternative to Scheme 5 for production of LEV derivatives, including an immunogenic derivative.
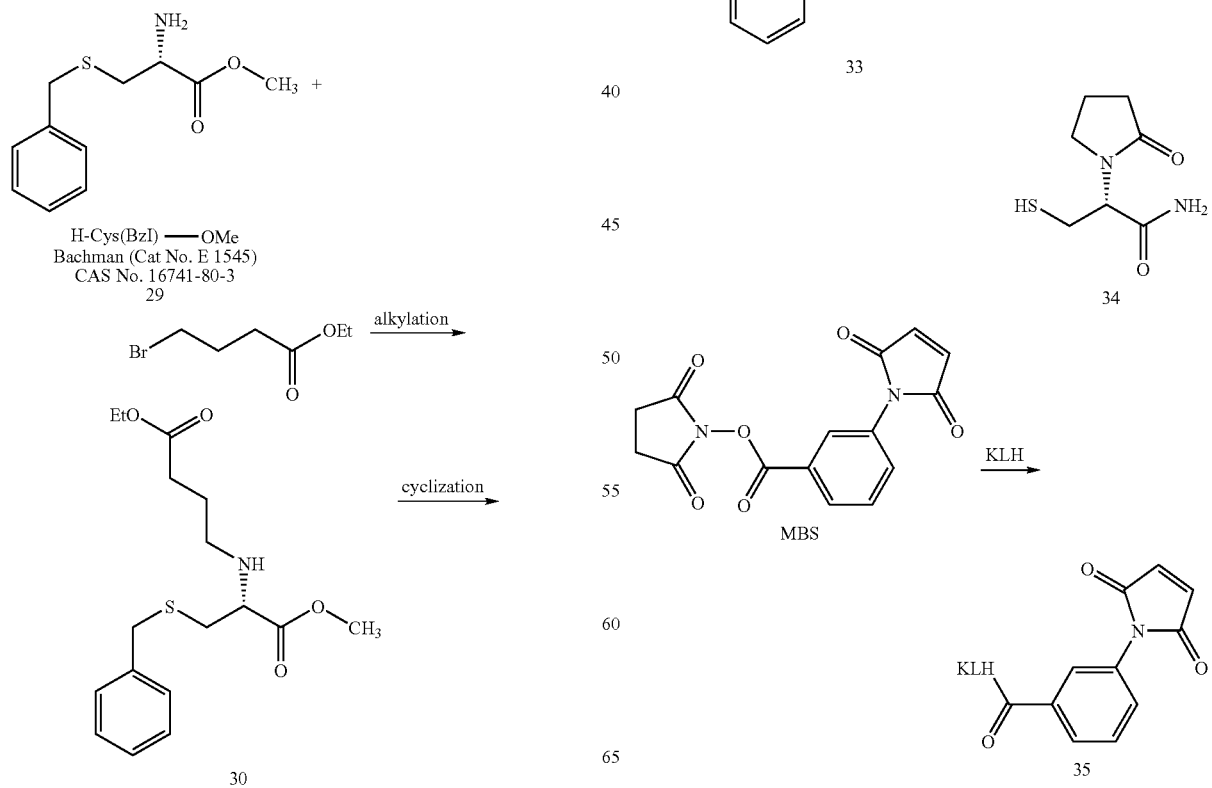

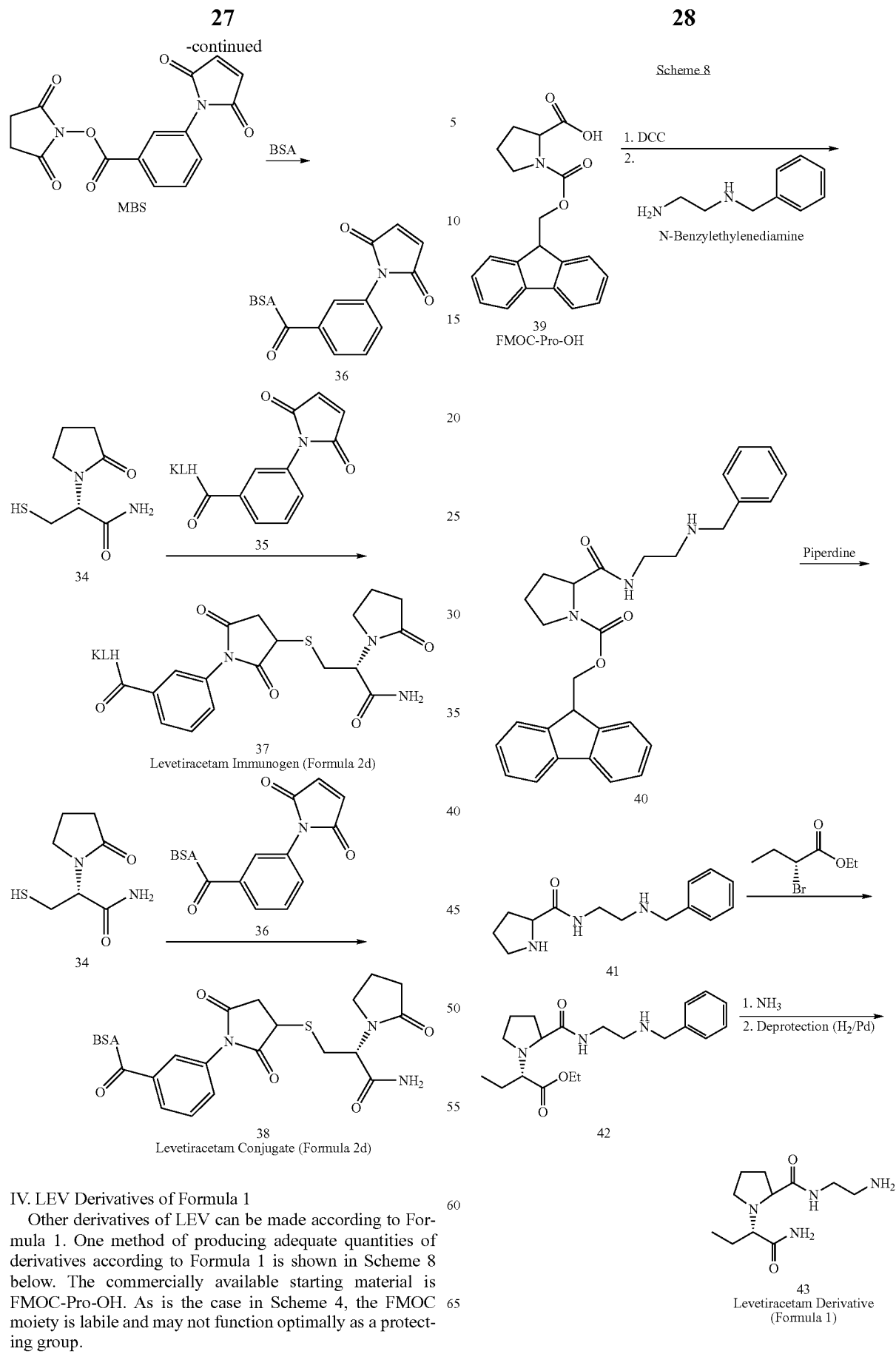
IV. LEV Derivatives of Formula 1
Other derivatives of LEV can be made according to Formula 1. One method of producing adequate quantities of derivatives according to Formula 1 is shown in Scheme 8 below. The commercially available starting material is FMOC-Pro-OH. As is the case in Scheme 4, the FMOC moiety is labile and may not function optimally as a protecting group.

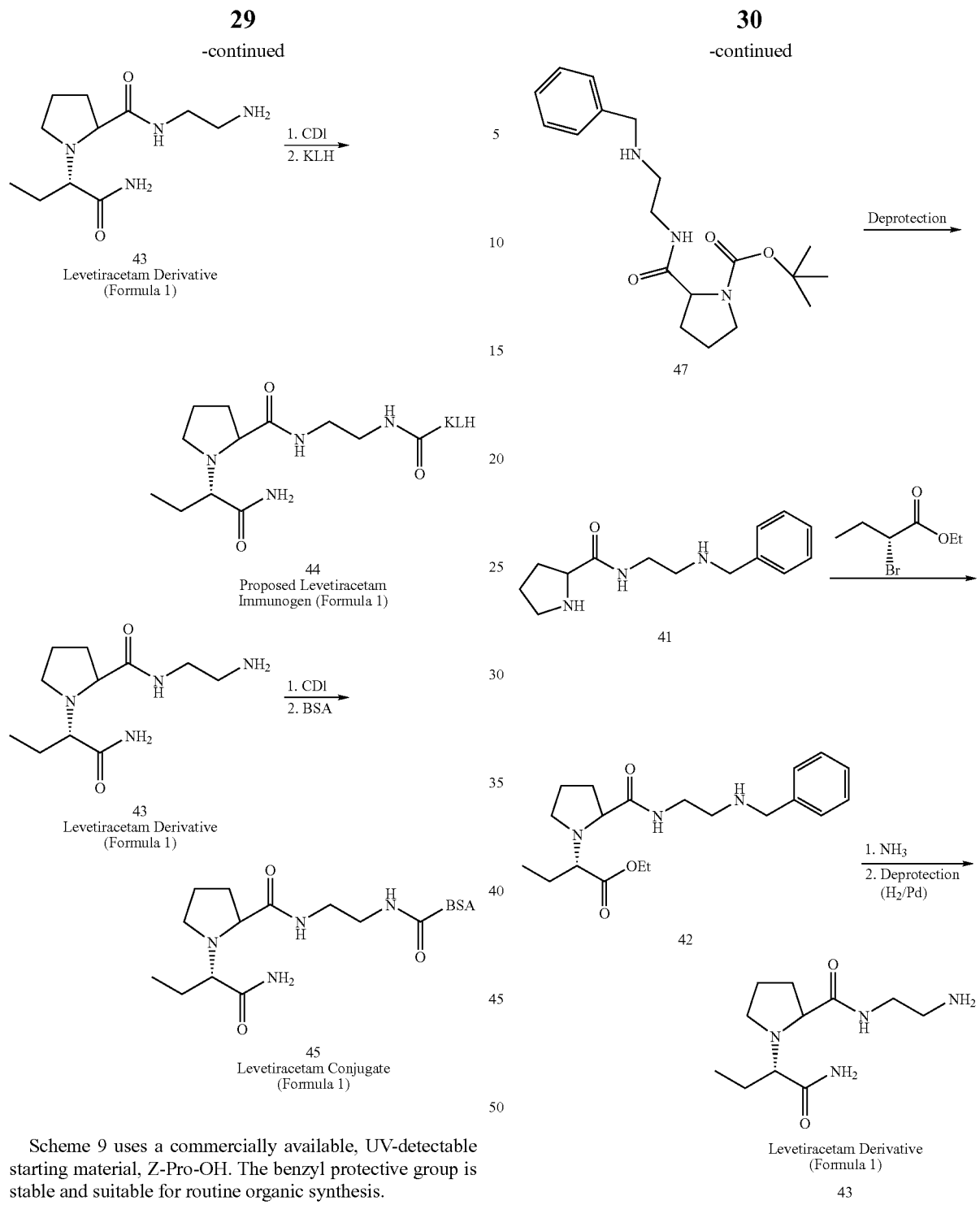
Scheme 9 uses a commercially available, UV-detectable starting material, Z-Pro-OH. The benzyl protective group is stable and suitable for routine organic synthesis.
Scheme 9

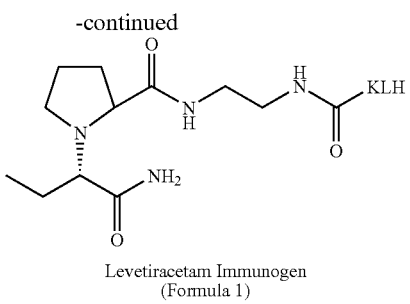

Levetiracetam Immunogen
(Formula 1)
44

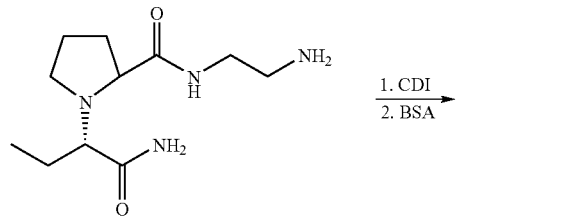

Levetiracetam Derivative
(Formula 1)
43

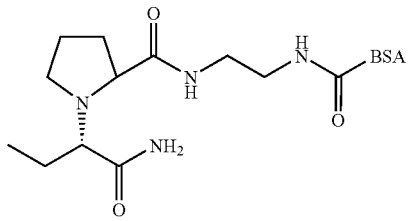

Levetiracetam Conjugute
(Formula 1)
45

Schemes 8 and 9 are suitable for producing derivatives of LEV, including immunogenic derivatives, useful for developing immunoassays for LEV.

V. Use of LEV Derivatives in Immunoassays

Immunogenic derivatives, for example, but not limited to, any of Compounds 18a, 27, 37 or 44, are useful for inducing anti-LEV antibody production as described in additional detail below. Other derivatives, for example, but not limited to, any of Compounds 18b, 28, 38, or 44, are useful for making antigens for competing with LEV in the specimen ("competitive antigen").

A competitive antigen and/or an anti-LEV antibody may be conjugated with a detectable label, as is known in the art. Detectable labels include, without limitation, dyes, latex particles, colloidal gold, fluorophores, chromophores, enzymes, enzyme fragments, radioactive isotopes, and the like.

A competitive antigen and/or an anti-LEV antibody may be immobilized on a solid surface, via covalent or non-covalent bonding. Solid surfaces include, without limitation: particles; porous materials, including membranes and filters; non-porous materials, including glass, metal, and non-porous plastics; and the like.

Anti-LEV antibodies and, optionally, competitive antigens comprise the essential reagents for a quantitative immunoassay for measuring levetiracetam concentrations. Immunoassays can include, but are not limited to, homogeneous microparticle immunoassay (e.g., immunoturbidimetric) or quantitative microsphere systems ("QMS®"), fluorescence polarization immunoassay ("FPIA"), chemiluminescent microparticle immunoassay ("CMIA"), cloned enzyme donor immunoassay ("CEDIA"), enzyme-linked immunoassay ("ELISA") and the like, as know in the art.

VI. EXAMPLES

The following examples are provided to illustrate embodiments of the prevention and are not intended to be limiting. Accordingly, some of the examples have been performed via experiment and some are prophetic based on techniques, standards, and results well known in the art. Also, it should be apparent that the invention can include additional embodiments not illustrated by example. Additionally, many of the examples have been performed with experimental protocols well known in the art using the LEV derivatives, antigens, immunogens, and anti-LEV antibodies prepared in accordance with the present invention.

Example 1

Scheme 5, Step1: Alkylation

Compound 10, H-Lys(Z)-Ot-Bu.HCl (NovaBiochem, Cat. No. 04-12-5122), 20.0065 g, was placed into a clean 500 mL single-neck round bottom. A magnetic stir bar was added to the reaction flask, and the flask was capped with a rubber septum and purged by argon for 15 min. 80 mL of anhydrous N,N-dimethylformamide was added to the reaction flask through the septum using clean syringe, such as a Hamilton Gastight® syringe. The reaction mixture was stirred under argon at ambient temperature for another 15 min. The reaction mixture was stirred under argon for 10 min at ambient temperature. 7.68 mL of ethyl 4-bromobutyrate was added to the flask drop-wise through the septum using a clean syringe. The reaction mixture was stirred under argon for 10 min at ambient temperature. A condenser with cold running tap water was mounted onto the reaction flask and the argon line was installed on the top of the condenser. The reaction flask was immersed into an oil bath preheated to 70° C. and stirred under argon for 40 h.

The reaction mixture was cooled to room temperature. Solvent (DMF) was evacuated using a rotary evaporator connected to a vacuum pump via a solvent trap. The desired product, Compound 11 was purified using column liquid chromatography with 1:3 acetone:chloroform used as an eluent. Isolated Compound 11 yields were 62-74%.

Example 2

Scheme 5, Step 2: Lactamization/Cyclization

Compound 11, 18.818 g, was transferred to a clean 250 mL single-neck round bottom flask (reaction flask). The flask was capped with a rubber septum and purged with argon for approximately 15 min. 61 mL of anhydrous toluene was added into the reaction flask through the septum using a clean syringe. The reaction mixture was stirred under argon at ambient temperature for about 10 min, then 1.169 g of 2-hydroxypyridine was added into the reaction flask as solid powder. The reaction mixture was stirred under argon for approximately 10 min at ambient temperature. A condenser with cool running tap water was mounted onto the reaction flask. The argon line was installed on top of the condenser. The reaction flask was immersed into an oil bath preheated to 120° C. and stirred under argon for about 15 h until the 2-hydroxypyridine was completely dissolved.

The reaction mixture was cooled to room temperature. Solvent (toluene) was evacuated on rotary evaporator connected to aspirator. The desired product, Compound 12 was purified using column liquid chromatography with 1:3 hexanes:ethyl acetate used as an eluent. The yields of Compound 12 ranged from 49-83%.

Example 3

Scheme 5, Step 3 Hydrolysis 14.019 g of Compound 12 was transferred into a clean 250 mL single-neck round bottom reaction flask. 50 mL of dichloromethane was added to the reaction flask using a clean graduated cylinder. The reaction mixture was stirred at ambient temperature for about 5 min, 102 mL of trifluoroacetic acid was added into the reaction flask using a clean graduated cylinder. The reaction flask was capped with a rubber septum and stirred at ambient temperature for approximately 4 h.

Solvent (dichloromethane) was evacuated using a rotary evaporator connected to an aspirator. The desired product, Compound 13 was purified using column liquid chromatography with 1:1 acetone:ethyl acetate used as an eluent. Yields of Compound 13 ranged from 66-92%.

Example 4

Scheme 5, Step 4: Activation

Compound 13, 11.074 g, was transferred to a jacketed 250 mL single-neck round bottom reaction flask connected to circular thermostat preset to 0° C. The reaction flask was capped with a rubber septum and purged with argon for approximately 15 min. 30 mL of anhydrous acetonitrile was added to the reaction flask through the septum using a clean syringe. The reaction mixture was stirred under argon at 0° C. for about another 15 min. 7.2 mL of N,N-diisopropylethylamine was added into the reaction flask slowly through the septum using a clean syringe. The reaction mixture was stirred under argon for about 10 min at 0° C.

11.15 g of TSTU (O—(N-Succinimidyl)-1,1,3,3-tetramethyl uranium tetrafluoroborate; ≥98%, Fluka, Cat. No. 85972) was completely dissolved in 50 mL of anhydrous acetonitrile. The resultant solution was added into the reaction flask through the septum using a clean syringe. The reaction mixture was stirred under argon for approximately 2.5 h at 0° C.

Solvent (acetonitrile) was removed using a rotary evaporator connected to an aspirator. The desired product, Compound 14, was purified using flash chromatography using Quick Separation Column/Funnel with fritted disc (ChemGlass Cat. No. CG-1412) with 1:9 hexanes:ethyl acetate used as an eluent. The product yields were 85-93%.

Example 5

Scheme 5, Step 5: Aminolysis 12.241 g of Compound 14 was transferred to a clean jacketed 250 mL single-neck round bottom reaction flask connected to circular thermostat preset to 0° C. The reaction flask was capped with a rubber septum and purged with argon for about 15 min. Upon addition of 110 mL of 7N ammonia in methanol (pre-chilled to about −20° C.), formation of white solid (N-hydroxysuccinimide) was observed. The reaction mixture was stirred under isolated conditions (capped with the rubber septum, without argon) for 2.5 h at 0° C. The reaction mixture was brought slowly to ambient temperature.

Unreacted ammonia and solvent (methanol) was removed using a rotary evaporator connected to an aspirator. Upon solvent removal, N-hydroxysuccinimide crystallized in the flask. Tetrahydrofuran (THF) was added to the reaction mixture and crystallized N-hydroxysuccinimide precipitated out of the solution. The crystals were removed by filtering through a fitted Buckner funnel. THF from the filtrate solution was removed via a rotary evaporator connected to an aspirator. The desired product, Compound 15 was purified using column liquid chromatography with 1:9 methanol:ethyl acetate used as an eluent with yields of about 60-70%.

Example 6

Scheme 5, Step 6: Deprotection

Compound 15, 1.5 g, was transferred into a clean 200 mL single-neck round bottom reaction flask. The reaction flask was capped with a rubber septum and purged by low flow of argon for approximately 15 min. 40 mL of absolute ethanol was added into the reaction flask using a clean syringe. The mixture was stirred under argon at ambient temperature for about 5 min and then 1.373 g of ammonium formate was added into the reaction flask as solid powder. The reaction mixture was stirred under argon for 5 min at ambient temperature, followed by addition of 11 mL of deionized water. Stirring continued under argon at ambient temperature for approximately 5 min until the ammonium formate completely dissolved. The reaction flask was immersed into an oil bath preheated to 110° C. and stirred under argon for about 7 h.

The desired product, Compound 3, was purified using Biotage® column liquid chromatography with 1:9 methanol: ethyl acetate used as an eluent. The isolated yields of Compound 3 were 50-70%.

Example 7

Scheme 5, Step 7: Aminolysis 70 mg of Compound 3 was dissolved uniformly in 3 mL of acetone in 10 mL conical flask. 2 mL of the solution was withdrawn and transferred using syringe into an empty clean 5 mL conical flask. Acetone was evaporated from the 5 mL flask using rotary evaporator.

3 mL of anhydrous N,N-dimethylformamide was added to the flask containing compound 3. 0.164 mL of N,N-diisopropylethylamine was added into the 5 mL conical flask slowly through the septum using clean syringe.

Separately, 760 mg of Compound 16 was placed into 200 mL single-neck round bottom flask (reaction flask). A magnetic stir bar was placed into the reaction flask. The reaction flask was capped with a rubber septum and was purged with argon for 15 min. 45 mL of anhydrous N,N-dimethylformamide was added into the reaction flask. 22 was thoroughly stirred and dissolved with mild sonication without heating in ultrasonic bath. The reaction flask was immersed into jacketed beaker filled with 1:1 water:ethylene glycol, and connected to circular thermostat preset to 0° C. Stirring under argon at 0° C. continued for another 10 min.

Compound 3 solution was added into the reaction flask containing Compound 16 dropwise over 10 min using a Hamilton Gastight® syringe. The syringe was rinsed with two 1 mL portions of anhydrous N,N-dimethylformamide and the rinses were added into the reaction flask. The reaction mixture was stirred under argon for 1 h at 0° C. The reaction flask was removed from cooling bath and allowed to reach room temperature. The reaction mixture was stirred at room temperature under argon for 6 h.

Solvent (N,N-dimethylformamide) was removed using a rotary evaporator connected to a vacuum pump through two solvent traps. The desired product, Compound 17, was purified using Biotage® column liquid chromatography with dichloromethane:acetone (starting from 100% dichloromethane and ending with 100% acetone) used as an eluent. Compound 17 yields were 23-39%.

Example 8

Scheme 5, Step 8: Preparation of Levetiracetam Immunogen

A solution of 160 mg of keyhole limpet hemocyanin (KLH) in 8 ml pH 7.2 PBS (0.1 M sodium phosphate, 0.15 M sodium chloride) was cooled in an ice bath. About 11.8 mL of DMSO was added to the KLH solution drop-wise, and maintained below room temperature. A solution of 30 mg of Compound 17 in 1.0 mL DMSO was added to the KLH solution drop-wise to form a reaction mixture and the mixture was allowed to stir at ambient temperature for approximately 40 h. The resulting immunogen (Compound 18a) was placed in a dialysis tube (10,000 MW cut-off), and serially dialyzed in 1 L of 30% DMSO in pH 7.2 PBS, followed by 1 L of 10% DMSO in pH 7.2 PBS, then 1 L of 5% DMSO in pH 7.2 PBS at room temperature, and then four changes with pH 7.2 PBS at 4° C. (1 L each for at least 6 hours each).

Example 9

Scheme 5, Step 9: Preparation of Levetiracetam Conjugate

A solution of 400 mg of bovine serum albumin (BSA) in 25 ml pH 7.2 PBS (0.1 M sodium phosphate, 0.15 M sodium chloride) was cooled in an ice bath. About 16 mL of DMSO was added to the BSA solution drop-wise, and maintained below room temperature.

A solution of 28 mg of Compound 3 in 1.0 mL anhydrous DMF, was added 0.2 mL anhydrous N,N-diisopropyl ethylamine. To a different round bottom flask, was added 48 mg of carbonyl diimidazole (CDI) and 1 mL anhydrous DMF.

The solution containing Compound 3 was added to the solution of CDI in DMF drop-wise via a syringe over a period of about 10 min and the resultant mixture was stirred in an ice bath for approximately 5 hours.

The solution of Compound 3/CDI was added to the BSA solution drop-wise using a syringe over a period of about 20 min. The resultant mixture was stirred overnight at 2-8 degree C. The resulting Compound 18b was placed in a dialysis tube (10,000 MW cut-off), and serially dialyzed in 1 L of 30% DMSO in pH 7.2 PBS, then 1 L of 10% DMSO in pH 7.2 PBS, followed by four changes with pH 7.2 PBS at 4° C. (1 L each for at least 6 hours each).

Example 10

Scheme 6, Step 1: Alkylation

Compound 20, H-Glu (OBzl)-OtBu (Bachem, Cat. No. E3535, CAS No. 105590-97-4), 5 g, was placed into a clean 100 mL single-neck round bottom. A magnetic stir bar was placed into the reaction flask, and the reaction flask was capped with a rubber septum and purged by argon for 15 min. 20 mL of anhydrous N,N-dimethylformamide was added to the reaction flask through the septum using a clean syringe. The reaction mixture was stirred under argon at ambient temperature for another 15 min and then 2 mL of ethyl 4-bromobutyrate was added to the flask drop-wise through the septum using a clean syringe. The reaction mixture was stirred under argon for about 10 min at ambient temperature. A condenser with cold running tap water was mounted onto the reaction flask and the argon line was installed on the top of the condenser. The reaction flask was immersed into an oil bath preheated to 70° C. and stirred under argon for approximately 40 h.

The reaction mixture was cooled to room temperature. Solvent (DMF) was evacuated using a rotary evaporator connected to a vacuum pump via a solvent trap. The evaporator condenser coil coolant (1:1 ethylene glycol:water) was pre-cooled to approximately −15° C. The desired product, Compound 21, was purified using column liquid chromatography with 1:3 acetone:chloroform used as an eluent. Isolated Compound 21 yields were 50-70%.

Example 11

Scheme 6, Step 2: Lactamization/Cyclization

Compound 21, 4 g, was transferred to a clean 100 mL single-neck round bottom flask (reaction flask). The flask was capped with a rubber septum and purged with argon for approximately 15 min. 15 mL of anhydrous toluene was added into the reaction flask through the septum using a clean syringe. The reaction mixture was stirred under argon at ambient temperature for about 10 min, then 0.3 g of 2-hydroxypyridine was added into the reaction flask as solid powder. The reaction mixture was stirred under argon for approximately 10 min at ambient temperature. A condenser with cool running tap water was mounted onto the reaction flask. The argon line was installed on top of the condenser. The reaction flask was immersed into an oil bath preheated to 120° C. and stirred under argon for about 15 h until the 2-hydroxypyridine was completely dissolved.

The reaction mixture was cooled to room temperature. Solvent (toluene) was evacuated on rotary evaporator connected to aspirator. The desired product, Compound 22, was purified using column liquid chromatography with 1:3 hexanes:ethyl acetate used as an eluent. The yields of Compound 22 ranged from 40-70%.

Example 12

Scheme 6, Step 3 Hydrolysis 2 g of Compound 22 was transferred to a clean 100 mL single-neck round bottom reaction flask. 10 mL of dichloromethane was added to the reaction flask using a clean graduated cylinder. The reaction mixture was stirred at ambient temperature for about 5 min and then 10 mL of trifluoroacetic acid was added into the reaction flask using a clean graduated cylinder. The reaction flask was capped with a rubber septum and stirred at ambient temperature for approximately 4 h.

Solvent (dichloromethane, trifluoroacetic acid) was evacuated using a rotary evaporator connected to an aspirator. The desired product, Compound 23, was purified using column liquid chromatography with 1:1 acetone:ethyl acetate used as an eluent. Yields of Compound 23 ranged from 70-90%.

Example 13

Scheme 6, Step 4: Aminolysis

Compound 23, 1.75 g, was transferred to a jacketed 100 mL single-neck round bottom reaction flask connected to circular thermostat preset to 0° C. The reaction flask was capped with a rubber septum and purged with argon for approximately 15 min. 5 mL of anhydrous acetonitrile was added to the reaction flask through the septum using a clean syringe. The reaction mixture was stirred under argon at 0° C. for about another 15 min. 2 mL of N,N-diisopropylethylamine was added into the reaction flask slowly through the septum using a clean syringe. The reaction mixture turned from light yellow to deeper yellow. The reaction mixture was stirred under argon for about 10 min at 0° C.

1.80 g of TSTU (O—(N-Succinimidyl)-1,1,3,3-tetramethyl uranium tetrafluoroborate) was completely dissolved in 10 mL of anhydrous acetonitrile. The resultant solution was added into the reaction flask through the septum using a clean syringe. The reaction mixture was stirred under argon for approximately 2.5 h at 0° C.

Solvent (acetonitrile) was removed using a rotary evaporator connected to an aspirator. The intermediate was purified using flash chromatography using Quick Separation.

1.6 g of the intermediate was transferred to a clean jacketed 100 mL single-neck round bottom reaction flask connected to circular thermostat preset to 0° C. The reaction flask was capped with a rubber septum and purged with argon for about 15 min. Upon addition of 20 mL of 7N ammonia in methanol (pre-chilled to about −20° C.), formation of white solid (N-hydroxysuccinimide) was observed. The reaction mixture was stirred at isolated conditions (capped with the rubber septum, no Argon) for about 2.5 h at 0° C. The reaction mixture was brought slowly to ambient temperature.

Unreacted ammonia and solvent (methanol) was removed using a rotary evaporator connected to an aspirator. Upon solvent removal, N-hydroxysuccinimide crystallized in the flask. Tetrahydrofuran (THF) was added to the reaction mixture and crystallized N-hydroxysuccinimide precipitated out of the solution. The crystals were removed by filtering through a fitted Buckner funnel. THF from the filtrate solution was removed via a rotary evaporator connected to an aspirator. The desired product, Compound 24, was purified using column liquid chromatography with 1:9 methanol:ethyl acetate used as an eluent with yields of about 50-60%.

Example 14

Scheme 6, Step 5: Deprotection

Compound 24, 1.5 g, was transferred into a clean 200 mL single-neck round bottom reaction flask. The reaction flask was capped with a rubber septum and purged by low flow of argon for approximately 15 min. 40 mL of absolute ethanol was added into the reaction flask using a clean syringe. The mixture was stirred under argon at ambient temperature for about 5 min and then 1.4 g of ammonium formate was added into the reaction flask as solid powder. The reaction mixture was stirred under argon for 5 min at ambient temperature, followed by addition of 10 mL of deionized water. Stirring continued under argon at ambient temperature for approximately 5 min until the ammonium formate completely dissolved. The reaction flask was immersed into an oil bath preheated to 110° C. and stirred under argon for about 7 h.

The desired product, Compound 25, was purified using column liquid chromatography with 1:9 methanol:ethyl acetate used as an eluent. Yields of Compound 25 were 50-70%.

Example 15

Scheme 6, Step 6: Activation

Compound 25, 1.90 g, was transferred to a jacketed 100 mL single-neck round bottom reaction flask connected to circular thermostat preset to 0° C. The reaction flask was capped with a rubber septum and purged with argon for approximately 15 min. 5 mL of anhydrous DMF was added to the reaction flask through the septum using a clean syringe. The reaction mixture was stirred under argon at 0° C. for about another 15 min. 2 mL of N,N-diisopropylethylamine was added into the reaction flask slowly through the septum using a clean syringe. The reaction mixture was stirred under argon for about 10 min at 0° C.

1.95 g of TSTU (O—(N-Succinimidyl)-1,1,3,3-tetramethyl uranium tetrafluoroborate) was completely dissolved in 5 mL of anhydrous DMF. The resultant solution was added into the reaction flask through the septum using a clean syringe. The reaction mixture stirred under argon for approximately 2.5 h at 0° C.

Solvent (DMF) was removed using a rotary evaporator connected to an aspirator. The desired product, Compound 26, was purified using flash chromatography. Compound 26 yields were 60-70%.

Example 16

Scheme 6, Step 7: Preparation of Levetiracetam Immunogen

A solution of 160 mg of keyhole limpet hemocyanin (KLH) in 8 ml pH 7.2 PBS (0.1 M sodium phosphate, 0.15 M sodium chloride) was cooled in an ice bath. About 11.8 mL of DMSO was added to the KLH solution drop-wise, and maintained below room temperature. A solution of 32 mg of Compound 26 in 1.0 mL DMSO was added to the KLH solution drop-wise to form a reaction mixture. The reaction mixture was allowed to stir at room temperature for 40 h. The resulting KLH immunogen 27 was placed in a dialysis tube (10,000 MW cut-off), and serially dialyzed in 1 L of 30% DMSO in pH 7.2 PBS, then 1 L of 10% DMSO in pH 7.2 PBS, then 1 L of 5% DMSO in pH 7.2 PBS at room temperature, followed by four changes with pH 7.2 PBS at 4° C. (1 L each for at least 6 hours each).

Example 17

Scheme 6, Step 7: Preparation of Levetiracetam Conjugate

A solution of 400 mg of bovine serum albumin (BSA) in 8 ml pH 7.2 PBS (0.1 M sodium phosphate, 0.15 M sodium chloride) was cooled in an ice bath. About 11.8 mL of DMSO was added to the BSA solution drop-wise, and maintained below room temperature. A solution of 32 mg of Compound 26 in 1.0 mL DMSO was added to the BSA solution drop-wise to form a reaction mixture. The reaction mixture was allowed to stir at room temperature for 40 h. The resulting BSA conjugate, Compound 28, was placed in a dialysis tube (10,000 MW cut-off), and serially dialyzed in 1 L of 30% DMSO in pH 7.2 PBS, then 1 L of 10% DMSO in pH 7.2 PBS, then 1 L of 5% DMSO in pH 7.2 PBS at room temperature, and then followed by four changes with pH 7.2 PBS at 4° C. (1 L each for at least 6 hours each).

Example 18

Scheme 7, Step 1: Alkylation

Compound 29, H-Cys (OBzl)-OMe (Bachem, Cat. No. E 1545, CAS No. 16741-80-3), 4.5 g, was placed into a clean 100 mL single-neck round bottom. The reaction flask was capped with a rubber septum and purged by argon for 15 min. 20 mL of anhydrous N,N-dimethylformamide was added to the reaction flask through the septum using clean syringe. The reaction mixture was stirred under argon at ambient temperature for approximately 15 min. 2 mL of ethyl 4-bromobutyrate was added to the flask drop-wise through the septum using a clean syringe. The reaction mixture was stirred under argon for 10 min at ambient temperature. A condenser with cold running tap water was mounted onto the reaction flask and the argon line was installed on the top of the condenser. The reaction flask was immersed into an oil bath preheated to 70° C. and stirred under argon for 40 h.

The reaction mixture was cooled to room temperature. Solvent (DMF) was evacuated using a rotary evaporator connected to a vacuum pump via a solvent trap. The evaporator condenser coil coolant (1:1 ethylene glycol:water) was pre-cooled to approximately −15° C. The desired product, Compound 30, was purified using column liquid chromatography with 1:3 acetone:chloroform used as an eluent. Isolated Compound 30 yields were 50-70%

Example 19

Scheme 7, Step 2: Lactamization/Cyclization

Compound 30, 3.9 g, was transferred to a clean 100 mL single-neck round bottom flask (reaction flask). The flask was capped with a rubber septum, and purged by for approximately 15 min, then 15 mL of anhydrous toluene was added into the reaction flask through the septum using a clean syringe. The reaction mixture was stirred under argon at ambient temperature for about 10 min, then 0.31 g of 2-hydroxypyridine was added into the reaction flask as solid powder. The reaction mixture was stirred under argon for approximately 10 min at ambient temperature. A condenser with cool running tap water was mounted onto the reaction flask. The argon line was installed on top of the condenser. The reaction flask was immersed into an oil bath preheated to 120° C. and stirred under argon for about 15 h until the 2-hydroxypyridine was completely dissolved.

The reaction mixture was cooled to room temperature. Solvent (toluene) was evacuated on rotary evaporator connected to aspirator. The desired product, Compound 31, was purified using column liquid chromatography with 1:3 hexanes:ethyl acetate used as an eluent. The yields of Compound 31 ranged from 50-70%.

Example 20

Scheme 7, Step 3 Hydrolysis 2.1 g of Compound 31 was transferred into a clean 100 mL single-neck round bottom reaction flask. 10 mL of methanol and 10 mL of deionized water were added to the reaction flask. 200 mg of LiOH was added to the flask. The reaction mixture was stirred at ambient temperature for about 4 h.

Solvent (methanol, water) was evacuated using a rotary evaporator connected to an aspirator. The desired product, Compound 32, was purified using column liquid chromatography with 1:1 acetone:ethyl acetate used as an eluent. Yields of Compound 32 ranged from 70-90%.

Example 21

Scheme 7, Step 4: Aminolysis

Compound 32, 1.80 g, was transferred to a jacketed 100 mL single-neck round bottom reaction flask connected to circular thermostat preset to 0° C. The reaction flask was capped with a rubber septum and purged with argon for approximately 15 min. 5 mL of anhydrous acetonitrile was added to the reaction flask through the septum using a clean syringe. The reaction mixture was stirred under argon at 0° C. for about another 15 min. 2 mL of N,N-diisopropylethylamine was added into the reaction flask slowly through the septum using a clean syringe. The reaction mixture turned from light yellow to deeper yellow. The reaction mixture was stirred under argon for about 10 min at 0° C.

1.85 g of TSTU (O—(N-Succinimidyl)-1,1,3,3-tetramethyl uranium tetrafluoroborate) was completely dissolved in 10 mL of anhydrous acetonitrile. The resultant solution was added into the reaction flask through the septum using a clean syringe and was stirred under argon for approximately 2.5 h at 0° C.

Solvent (acetonitrile) was removed using a rotary evaporator connected to an aspirator. The intermediate was purified using flash chromatography using Quick Separation.

1.62 g of the intermediate was transferred to a clean jacketed 100 mL single-neck round bottom reaction flask connected to circular thermostat preset to 0° C. The reaction flask was capped with a rubber septum and purged with argon for about 15 min. Upon addition of 20 mL of 7N ammonia in methanol (pre-chilled to about −20° C.), formation of white solid (N-hydroxysuccinimide) was observed. The reaction mixture was stirred at isolated conditions (capped with the rubber septum, no Argon) for 2.5 h at 0° C. The reaction mixture was brought slowly to ambient temperature.

Unreacted ammonia and solvent (methanol) was removed using a rotary evaporator connected to an aspirator The desired product, Compound 33, was purified using column liquid chromatography with 1:9 methanol:ethyl acetate used as an eluent with yields of about 50-60%.

Example 22

Scheme 7, Step 5: Deprotection

Compound 33, 1.51 g, was transferred into a clean 200 mL single-neck round bottom reaction flask. The reaction flask was capped with a rubber septum and purged by low flow of argon for approximately 15 min. 40 mL of absolute ethanol was added into the reaction flask using a clean syringe. The mixture was stirred under argon at ambient temperature for about 5 min and then 1.4 g of ammonium formate was added into the reaction flask as solid powder. The reaction mixture was stirred under argon for 5 min at ambient temperature, followed by addition of 10 mL of deionized water. Stirring continued under argon at ambient temperature for approximately 5 min until the ammonium formate completely dissolved. The reaction flask was immersed into an oil bath preheated to 110° C. and stirred under argon for about 7 h.

The desired product, compound 34, was purified using column liquid chromatography with 1:9 methanol:ethyl acetate used as an eluent. Yields of Compound 34 were 50-70%.

Example 23

Scheme 7, Step 7: Preparation of Levetiracetam Immunogen

A solution of 60 mg of keyhole limpet hemocyanin (KLH) in 3 ml pH 7.2 PBS (0.1 M sodium phosphate, 0.15 M sodium chloride) was cooled in an ice bath. 10.2 mg of m-maleimidobenzoyl-N-hydroxysuccinimide ester (MBS), a heterobifunctional crosslinking agent containing an NHS ester on one end and a melaimide group on the other end, was dissolved in 0.5 mL DMSO and the MBS solution was added to KLH solution dropwise while chilled in an ice bath. The reaction mixture was stirred in an ice bath for 4 h. The KLH-MBS conjugate was purified via PD-10 desalting column (to remove the excess MBS).

10.2 mg of compound 34 was dissolved in 0.5 mL DMSO and the resulting solution was added to the purified KLH-MBS solution drop-wise while chilled in an ice bath. The mixture was stirred at room temperature for 2 h. The resulting immunogen, Compound 37, is placed in a dialysis tube (10,000 MW cut-off), and serially dialyzed in 1 L of 30% DMSO in pH 7.2 PBS, then 1 L of 10% DMSO in pH 7.2 PBS, then 1 L of 5% DMSO in pH 7.2 PBS at room temperature, followed by four changes with pH 7.2 PBS at 4° C. (1 L each for at least 6 hours each).

Example 24

Scheme 7, Step 8: Preparation of Levetiracetam Conjugate

A solution of 100 mg of bovine serum albumin (BSA) in 5 ml pH 7.2 PBS (0.1 M sodium phosphate, 0.15 M sodium chloride) is cooled in an ice bath. 10.2 mg of MBS was dissolved in 0.5 mL DMSO and the MBS solution was then added to BSA solution drop-wise while chilled in an ice bath. The reaction mixture was allowed to stir in an ice bath for 4 h. The BSA-MBS conjugate was purified via PD-10 desalting column (to remove the excess MBS).

12.3 mg of compound 34 was dissolved in 0.5 mL DMSO and the resulting solution was added to the purified BSA-MBS solution drop-wise while chilled in an ice bath. The mixture was stirred at room temperature for 2 h. The resulting conjugate, Compound 38, was placed in a dialysis tube (10,000 MW cut-off), and serially dialyzed in 1 L of 30% DMSO in pH 7.2 PBS, then 1 L of 10% DMSO in pH 7.2 PBS, then 1 L of 5% DMSO in pH 7.2 PBS at room temperature, followed by four changes with pH 7.2 PBS at 4° C. (1 L each for at least 6 hours each).

Example 25

Scheme 8, Step 1: Nucleophilic Acyl Addition 210 mg of Compound 39, FMOC-Pro-OH(N-9-Fluorenylmethoxycarbonyl)-L-proline, Aldrich Cat No. 33834-6), 70 mg N-hydroxysuccinimide (NHS) and 2 mL anhydrous DMF were placed in a 100 mL round bottom flask with a magnetic stirrer. The mixture was chilled on an ice-methanol bath and treated with 0.2 mL of 3.5 M DCC (dicyclohexycarbodiimide in DMF). The reaction mixture was stirred in the ice-methanol bath for 15 min under argon and another 0.1 mL of DCC solution was added. The mixture was while slowly brought to room temperature and then stirred at room temperature overnight while under argon.

1 mL of N-benzylethylenediamine and 5 mL anhydrous DMF were placed in a reaction flask with a magnetic stirrer. The flask was capped with a rubber septum and purged with argon for about 15 min. Activated FMOC-Pro-OH in DMF solution was added slowly to the N-benzylethylenediamine in DMF solution via a syringe. The reaction mixture was stirred under argon at ambient temperature for another 6 h.

Solvent (DMF) was evacuated using a rotary evaporator connected to a vacuum pump via a solvent trap. The evaporator condenser coil coolant (1:1 ethylene glycol:water) was precooled to approximately −15° C. The desired product, Compound 40, was purified using column liquid chromatography with 1:9 hexane:chloroform used as an eluent. Isolated Compound 40 yields were 60-70%.

Example 26

Scheme 8, Step 2: Deprotection

Compound 40, 200 mg was transferred to a clean 100 mL single-neck round bottom flask (reaction flask). 10 mL of anhydrous DMF and 5 mL piperidine were added into the reaction flask and the reaction mixture was stirred under argon for 4 h at ambient temperature.

Solvent (DMF, piperidine) was evacuated on rotary evaporator connected to aspirator. The desired product, Compound 41, was purified using column liquid chromatography with 2:8 methanol:methylene chloride (dichloromethane) used as an eluent. The yields of Compound 41 ranged from 50-70%.

Example 27

Scheme 8, Step 3: Alkylation

Compound 41 was placed into a clean 100 mL single-neck round bottom. The reaction flask was capped with a rubber septum and purged with argon for 15 min. 20 mL of anhydrous N,N-dimethylformamide was added to the reaction flask through the septum using clean syringe and the reaction mixture was stirred under argon at ambient temperature for another 15 min. 2 mL of ethyl 2-bromobutyrate was added to the flask drop-wise through the septum using a clean syringe. The reaction mixture was stirred under argon for 10 min at ambient temperature. A condenser with cold running tap water was mounted onto the reaction flask and the argon line was installed on the top of the condenser. The reaction flask was immersed in an oil bath preheated to 70° C. and stirred under argon for 40 h.

The reaction mixture was cooled to room temperature. Solvent (DMF) was evacuated using a rotary evaporator connected to a vacuum pump via a solvent trap. The evaporator condenser coil coolant (1:1 ethylene glycol:water) was precooled to approximately −15° C. The desired product, Compound 42, was purified using column liquid chromatography with 1:3 acetone:chloroform used as an eluent. Isolated Compound 42 yields were 50-70%.

Example 28

Scheme 8, Step 4: Deprotection

To 20 mL of concentrated ammonium hydroxide, was added 2.0 g of compound 42 and 0.1 g ammonium chloride.

The mixture was heated at 100° C. for approximately 7 h with stirring and then cooled to room temperature. The resulting precipitate was filtered and washed with water and diethyl ether. Yield of the intermediate were 60-70%.

1.0 g of the intermediate was transferred into a clean 100 mL single-neck round bottom reaction flask. The reaction flask was capped with a rubber septum and purged under a low flow of argon for approximately 15 min. 20 mL of absolute ethanol was added to the reaction flask using a clean syringe. The mixture was stirred under argon at ambient temperature for about 5 min and then 0.8 g of ammonium formate was added into the reaction flask as solid powder. The reaction mixture was stirred under argon for 5 min at ambient temperature, followed by addition of 5 mL of deionized water. Stirring continued under argon at ambient temperature for approximately 5 min until the ammonium formate completely dissolved. The reaction flask was immersed into an oil bath preheated to 110° C. and stirred under argon for about 7 h.

The desired product, compound 43, was purified using column liquid chromatography with 1:9 methanol:ethyl acetate used as an eluent. The isolated desired product yields were approximately 50%.

Example 29

Scheme 8, Step 5: Preparation of Levetiracetam Immunogen

A solution of 160 mg of KLH in 8 ml pH 7.2 PBS (0.1 M sodium phosphate, 0.15 M sodium chloride) was cooled in an ice bath. About 12 mL of DMSO was added to the KLH solution drop-wise, and maintained below room temperature.

A solution of 29 mg of Compound 43 in 1.0 mL anhydrous DMF, was added 0.2 mL anhydrous N,N-diisopropyl ethylamine. To a separate round bottom flask, was added 48 mg of CDI (carbonyl diimidazole) and 1 mL anhydrous DMF.

The solution containing Compound 43 was added to the CDI/DMF solution via a syringe drop-wise over a period of about 10 min and then stirred in an ice bath for approximately 5 hours.

The Compound 43/CDI solution was to the KLH solution drop-wise using a syringe over 20 min. The mixture was stirred overnight at 2-8 degree C. The resulting immunogen, Compound 44, was placed in a dialysis tube (10,000 MW cut-off), and serially dialyzed in 1 L of 30% DMSO in pH 7.2 PBS, then 1 L of 10% DMSO in pH 7.2 PBS, followed by four changes with pH 7.2 PBS at 4° C. (1 L each for at least 6 hours each).

Example 30

Scheme 8, Step 6: Preparation of Levetiracetam Conjugate

A solution of 400 mg of bovine serum albumin (BSA) in 25 ml pH 7.2 PBS (0.1 M sodium phosphate, 0.15 M sodium chloride) was cooled in an ice bath. About 16 mL of DMSO was added to the KLH solution drop-wise, and maintained below room temperature.

A solution of 28 mg of Compound 43 in 1.0 mL anhydrous DMF, was added 0.2 mL anhydrous N,N-diisopropyl ethylamine. To a separate round bottom flask was added 48 mg of carbonyl diimidazole (CDI) and 1 mL anhydrous DMF.

The solution containing Compound 43 was added to the CDI/DMF solution via a syringe drop-wise over a period of 10 min and then stirred in an ice bath for about 5 hours.

The solution was then added to the protein solution drop-wise using a syringe over 20 min. The mixture was stirred overnight at 2-8 degree C. The resulting levetiracetam conjugate, Compound 45, was placed in a dialysis tube (10,000 MW cut-off), and serially dialyzed in 1 L of 30% DMSO in pH 7.2 PBS, then 1 L of 10% DMSO in pH 7.2 PBS, followed by four changes with pH 7.2 PBS at 4° C. (1 L each for at least 6 hours each).

Example 31

Scheme 9, Step 1: Nucleophilic Acyl Addition 205 mg of Compound 46, BOC-Pro-OH (N-9-Fluorenyl-methoxycarbonyl)-L-proline, Bachem Cat No. A-2235, 70 mg N-hydroxysuccinimide (NHS) and 2 mL anhydrous DMF were placed in a 100 mL round bottom flask with a magnetic stirrer. The mixture was chilled on an ice-methanol bath and treated with 0.2 mL of 3.5 M DCC (dicyclohexycarbodiimide in DMF) and then stirred in the ice-methanol bath for 15 min under argon, followed by the addition of another 0.1 mL of DCC solution. Stirring continued while the reaction mixture was slowly brought to room temperature. The reaction mixture was stirred at room temperature overnight under argon.

1 mL of N-benzylethylenediamine and 5 mL anhydrous DMF were placed in a reaction flask with a magnetic stirrer. The flask was capped with a rubber septum and purged by argon for 15 min. Activated FMOC-Pro-OH in DMF solution was added slowly to the N-benzylethylenediamine in DMF solution via a syringe. The reaction mixture was stirred under argon at ambient temperature for another 6 h.

Solvent (DMF) was evacuated using a rotary evaporator connected to a vacuum pump via a solvent trap. The evaporator condenser coil coolant (1:1 ethylene glycol:water) was precooled to approximately −15° C. The desired product, Compound 47, was purified using column liquid chromatography with 1:9 hexane:chloroform used as an eluent. Isolated Compound 47 yields were 65-75%

Example 32

Scheme 9, Step 2: Deprotection 200 mg of Compound 47 was transferred into a clean 100 mL single-neck round bottom reaction flask. 25 mL of dichloromethane was added to the reaction flask using a clean graduated cylinder. The reaction mixture was stirred at ambient temperature for about 5 min, 25 mL of trifluoroacetic acid was added into the reaction flask using a clean graduated cylinder. The reaction flask was capped with a rubber septum and stirred at ambient temperature for approximately 4 h.

Solvent (dichloromethane) was evacuated using a rotary evaporator connected to an aspirator. The desired product, Compound 41 was purified using column liquid chromatography with 2:8 methanol:methylene chloride (dichloromethane) used as an eluent. The yields of Compound 41 ranged from 50-70%.

Example 33

Scheme 8, Step 3: Alkylation

Compound 41 was placed into a clean 100 mL single-neck round bottom. The reaction flask was capped with a rubber septum and purged with argon for 15 min. 20 mL of anhydrous N,N-dimethylformamide was added to the reaction flask through the septum using clean syringe and the reaction mixture was stirred under argon at ambient temperature for another 15 min. 2 mL of ethyl 2-bromobutyrate was added to the flask drop-wise through the septum using a clean syringe. The reaction mixture was stirred under argon for 10 min at ambient temperature. A condenser with cold running tap water was mounted onto the reaction flask and the argon line was installed on the top of the condenser. The reaction flask was immersed in an oil bath preheated to 70° C. and stirred under argon for 40 h.

The reaction mixture was cooled to room temperature. Solvent (DMF) was evacuated using a rotary evaporator connected to a vacuum pump via a solvent trap. The evaporator condenser coil coolant (1:1 ethylene glycol:water) was pre-cooled to approximately −15° C. The desired product, Compound 42, was purified using column liquid chromatography with 1:3 acetone:chloroform used as an eluent. Isolated Compound 42 yields were 50-70%.

Example 34

Scheme 8, Step 4: Deprotection

To 20 mL of concentrated ammonium hydroxide, was added 2.0 g of compound 42 and 0.1 g ammonium chloride. The mixture was heated at 100° C. for approximately 7 h with stirring and then cooled to room temperature. The resulting precipitate was filtered and washed with water and diethyl ether. Yield of the intermediate were 60-70%.

1.0 g of the intermediate was transferred into a clean 100 mL single-neck round bottom reaction flask. The reaction flask was capped with a rubber septum and purged under a low flow of argon for approximately 15 min. 20 mL of absolute ethanol was added to the reaction flask using a clean syringe. The mixture was stirred under argon at ambient temperature for about 5 min and then 0.8 g of ammonium formate was added into the reaction flask as solid powder. The reaction mixture was stirred under argon for 5 min at ambient temperature, followed by addition of 5 mL of deionized water. Stirring continued under argon at ambient temperature for approximately 5 min until the ammonium formate completely dissolved. The reaction flask was immersed into an oil bath preheated to 110° C. and stirred under argon for about 7 h.

The desired product, compound 43, was purified using column liquid chromatography with 1:9 methanol:ethyl acetate used as an eluent. The isolated desired product yields were approximately 50%.

Example 35

Scheme 8, Step 5: Preparation of Levetiracetam Immunogen

A solution of 160 mg of KLH in 8 ml pH 7.2 PBS (0.1 M sodium phosphate, 0.15 M sodium chloride) was cooled in an ice bath. About 12 mL of DMSO was added to the KLH solution drop-wise, and maintained below room temperature.

A solution of 29 mg of Compound 43 in 1.0 mL anhydrous DMF, was added 0.2 mL anhydrous N,N-diisopropyl ethylamine. To a separate round bottom flask, was added 48 mg of CDI (carbonyl diimidazole) and 1 mL anhydrous DMF.

The solution containing Compound 43 was added to the CDI/DMF solution via a syringe drop-wise over a period of about 10 min and then stirred in an ice bath for approximately 5 hours.

The Compound 43/CDI solution was to the KLH solution drop-wise using a syringe over 20 min. The mixture was stirred overnight at 2-8 degree C. The resulting immunogen, Compound 44, was placed in a dialysis tube (10,000 MW cut-off), and serially dialyzed in 1 L of 30% DMSO in pH 7.2 PBS, then 1 L of 10% DMSO in pH 7.2 PBS, followed by four changes with pH 7.2 PBS at 4° C. (1 L each for at least 6 hours each).

Example 36

Scheme 8, Step 6: Preparation of Levetiracetam Conjugate

A solution of 400 mg of bovine serum albumin (BSA) in 25 ml pH 7.2 PBS (0.1 M sodium phosphate, 0.15 M sodium chloride) was cooled in an ice bath. About 16 mL of DMSO was added to the KLH solution drop-wise, and maintained below room temperature.

A solution of 28 mg of Compound 43 in 1.0 mL anhydrous DMF, was added 0.2 mL anhydrous N,N-diisopropyl ethylamine. To a separate round bottom flask was added 48 mg of carbonyl diimidazole (CDI) and 1 mL anhydrous DMF.

The solution containing Compound 43 was added to the CDI/DMF solution via a syringe drop-wise over a period of 10 min and then stirred in an ice bath for about 5 hours.

The solution was then added to the protein solution drop-wise using a syringe over 20 min. The mixture was stirred overnight at 2-8 degree C. The resulting levetiracetam conjugate, Compound 45, was placed in a dialysis tube (10,000 MW cut-off), and serially dialyzed in 1 L of 30% DMSO in pH 7.2 PBS, then 1 L of 10% DMSO in pH 7.2 PBS, followed by four changes with pH 7.2 PBS at 4° C. (1 L each for at least 6 hours each).

Example 37

Antibody Production

A polyclonal antibody that specifically binds with LEV is prepared using an immunogen as described above. More particularly, the immunogens 18a, 27, 37, and 44 having the KLH immunogenic moiety are used to generate anti-levetiracetam polyclonal antibody. An immunogenic composition is prepared by mixing about 0.5 mL of an immunogen-containing composition with about 0.5 mL of Freund's adjuvant. The resulting 1 mL immunogenic cocktail is then injected an animal, such as a sheep, goat, rabbit or other mammal. Subsequent immunogenic injections using a similar immunogenic cocktail are administered to the animal approximately every four weeks in order to induce production of anti-levetiracetam polyclonal antibodies.

Antibody composition can include an anti-levetiracetam antibody having at least one binding domain, wherein the antibody is capable of binding LEV present in a patient specimen and or binding a LEV derivative. Also, the antibody can be present in a titer of at least about 1:5,000, or at least about 1:10,000, or at least about 1:50,000, or at least about 1:100,000, or at least about 1:300,000. Depending upon the assay conditions, it can be preferable to have an antibody titer as low as 1:5,000 or as high as 1:300,000.

Additionally, the antibody can be a monoclonal antibody or a polyclonal antibody. The antibody can have at least one of affinity, specificity, or avidity for an LEV derivative compared to LEV that is sufficient for use in a homogeneous, heterogeneous, or other immunodiagnostic assay. As such, the interaction between the antibody and LEV derivative can be at least 50% of at least one of affinity, specificity, or avidity of the antibody for LEV present in a patient specimen, even more preferably at least 70% of at least one of affinity, specificity, or avidity of the antibody for LEV, most preferably at least 90% of at least one of affinity, specificity, or avidity of the antibody for LEV. Optionally, at least one of affinity, specificity, or avidity of the antibody for LEV derivative is substantially the same as for LEV.

Example 38

Determination of Antibody Titer

Antibodies were screened by performance in ELISA immunoassay as is know in the art. Multi-well plates for use in an ELISA assay were prepared to test the polyclonal antibodies prepared as described in Example 37. Levetiracetam derivatives, namely Compounds 18b and 19, were used as antigens for binding the antibodies by coating the LEV derivatives on the bottom of wells in different multi-well plates before exposure to anti-levetiracetam antibodies. More particularly, the levetiracetam derivatives were diluted in coating buffer, and then added to the wells of multi-well plate. After incubation for about 60 min at 37° C., the solvent in the coating buffer was decanted and a blocking buffer containing BSA or casein was added to the plate. The plate was incubated again for 60 min at 37° C., and the solvent in the blocking buffer decanted from the plate. Some ELISA plates were used within a few hours after preparation while others were stored for up to 1 week at 2-8° C. with blocking solution in the wells.

Antibody titer for a polyclonal antibody prepared in accordance with Example 37, specifically with immunogen 18a, was determined using ELISA plates as prepared above. Serial dilutions of the antibody were prepared between 1:10 and 1:2000, in 10-fold increments, in PBS at pH 7.4 and containing 0.1% BSA. A 100 μL volume of each dilution was added to separate wells on the ELISA plate. The plate was incubated for approximately 60 min at 37° C., and washed three times with 250 μL of PBS at pH 7.4 with 0.05% Tween 20. Next, 125 μL of a enzyme-conjugated secondary antibody (an anti-sheep IgG antibody) in PBS at pH 7.4 and containing 0.1% BSA was added to each well of the plate. Alternatively, the anti-levetiracetam antibody may be directly conjugated to an enzyme or other detectable label and the step of adding a enzyme-labeled second antibody may be eliminated. The plate was incubated for approximately 60 min at 37° C. The wells of the plate were washed as described above. After washing, about 125 μL of ABTS substrate was added to each well, and the multi-well plate was incubated again for 20 min. Absorbance values were obtained using a multi-well plate reader at a wavelength of 405 nm and the titer values were calculated. Titer results are provided in Table 3.

TABLE 3

| | | ELISA Titer | |
|---|---|---|---|
| Sheep No. | Immunogen | Antigen 18b | Antigen 19 |
| 5433 | 18a | 62000 | 75600 |
| 5478 | 18a | 151000 | 147000 |
| 5479 | 18a | 73500 | 68200 |

Example 39

Determination of Antibody Avidity

The avidity of the anti-levetiracetam antibody prepared with immunogen 18a for various levetiracetam derivatives were determined by a binding inhibition study. Samples were prepared in 1 mL of PBS at pH 7.4 with 0.1% BSA. A composition having 30% Bmax titer or 50% Bmax titer was used to divide the titer value as obtained in Example 38 into approximately half the titer value. Using 30% Bmax, an antibody titer of 1:10000 was diluted to 1:5000 during the sample preparation stage. About 50 μL of levetiracetam at different concentrations or calibrator values, (0, 5, 10, 20, 40, 80 μg/ml) were applied to a plate as prepared in accordance with Example 38. About 50 μL of the diluted antibody was dispensed into the plate, and the compositions in the plate were mixed for 1 min on a horizontal plate shaker. No levetiracetam or anti-levetiracetam antibody was added to the first row of the plate, which served as a negative control. A second row with anti-levetiracetam antibody but without levetiracetam was used as the positive control. The plate was incubated for 60 min and washed three times with 250 μL of PBS at pH 7.4 with 0.05% Tween 20. About 125 μL of a diluted derivative such as 18b or 19 in PBS at pH 7.4 was added to each well of the plate. The plate was incubated for 60 min at 37° C. and washed as described above. Approximately 125 μL of ABTS substrate was added to each well of the plate and incubated for 20 min. Absorbance values were obtained using a multi-well plate reader at 405 nm, and the results are provided in Table 4.

TABLE 4

| Sheep No. 5479 | Antigen 18b | | Antigen 19 | |
|---|---|---|---|---|
| Levetiracetam (μg/mL) | Abs. | B/Bo | Abs. | B/Bo |
| 0 | 0.83 | 1.00 | 0.86 | 1.00 |
| 5 | 0.80 | 0.96 | 0.84 | 0.98 |
| 10 | 0.81 | 0.98 | 0.78 | 0.91 |
| 20 | 0.75 | 0.90 | 0.74 | 0.86 |
| 40 | 0.73 | 0.88 | 0.67 | 0.78 |
| 80 | 0.72 | 0.87 | 0.66 | 0.77 |

As used herein, the term "hapten" is meant to refer to a partial or incomplete antigen, and can be a small molecule or drug. Also, a hapten can be a low molecular weight molecule that is a protein-free or polypeptide-free substance. Usually, a hapten is not capable of stimulating antibody formation alone, but can be capable of interacting with antibodies. Accordingly, LEV and LEV derivatives in accordance with the present invention can be haptens.

As used herein, the term "analog" or "derivative" is meant to refer to a chemical compound or molecule made from a parent compound or molecule by one or more chemical reactions. As such, an analog can be a compound with a structure similar to that of LEV or based on a LEV scaffold, but differing from it in respect to certain components or structural makeup, which may have a similar or opposite action metabolically. An analog or derivative of LEV in accordance with the present invention can be used to compete for binding with an antibody that recognize both the analog and LEV. Also, an analog can include an operative group coupled to LEV through a linker group.

As used herein, the term "antigen" is meant to refer to a molecule that is capable of being recognized by an antibody or another immune system component.

As used herein, the terms "immunogen" and "immunogenic" are meant to refer to substances capable of producing or generating an immune response in an organism. An immunogen is generally considered to be a specific type of antigen. Said another way, an immunogen is able to induce an immune response, while an antigen is able to combine with the products of an immune response once they are made. As such, an immunogen can also be antigen. Usually, an immunogen has a fairly high molecular weight (e.g., greater than about 10,000 Daltons), thus, a variety of macromolecules such as proteins, lipoproteins, polysaccharides, some nucleic acids, and certain of the teichoic acids, can be coupled to a hapten in order to form an immunogen in accordance with the present invention.

As used herein, the term "immunogenicity" is meant to refer to the ability of a molecule to induce an immune response, which is determined both by the intrinsic chemical structure of the injected molecule and by whether or not the host animal can recognize the compound. Small changes in the structure of an antigen can greatly alter the immunogenicity of a compound, and have been used extensively as a general procedure to increase the chances of raising an antibody, particularly against well-conserved antigens. For example, these modification techniques either alter regions of the immunogen to provide better sites for T-Cell binding or expose new epitopes for B-cell binding.

As used herein, the terms "carrier," "immunogenic moiety," or "immunogenic carrier," are meant to refer to an operative group that is an immunogenic substance, commonly a protein, that can be coupled to a hapten. An immunogenic moiety coupled to a hapten can induce an immune response and elicit the production of antibodies that can bind specifically with the hapten. Immunogenic moieties are operative groups that include proteins, polypeptides, glycoproteins, complex polysaccharides, particles, nucleic acids, polynucleotides, and the like that are recognized as foreign and thereby elicit an immunologic response from the host. Additionally, linkers can comprise modified or unmodified nucleotides, nucleosides, polymers, sugars and other carbohydrates, polyethers such as, for example, polyethylene glycols, polyalcohols, polypropylenes, propylene glycols, mixtures of ethylene and propylene glycols, polyalkylamines, polyamines such as spermidine, polyesters such as poly(ethyl acrylate), polyphosphodiesters, and alkylenes. An example of an operative group and its linker is cholesterol-TEG-phosphoramidite, wherein the cholesterol is the operative group and the tetraethylene glycol and phosphate serve as linkers.

In one example, an operative group is an immunogenic carrier that can be coupled with a hapten in order to stimulate immunogenicity and antibody formation against the hapten. Usually, immunogenic carriers are large molecules that are highly immunogenic and capable of imparting immunogenicity to a hapten. For example, a protein can be used as an immunogenic carrier because foreign proteins can elicit such an immunological response. Protein carriers can be highly soluble and include functional groups that could facilitate easy conjugation with a hapten molecule. Some of the most common carrier proteins in use today are keyhole limpet hemocyanin (KLH; MW 450,000 to 13,000,000), and bovine serum albumin (BSA, MW 67,000). Keyhole limpet hemocyanin is the oxygen-carrying protein of the marine keyhole limpet, and is extremely large and exhibits increased immunogenicity when it is disassociated into subunits, probably due to exposure of additional epitopic sites to the immune system. BSA is highly soluble protein containing numerous functional groups suitable for conjugation.

As used herein, the term "antibody" is meant to refer to a protein that is produced in response to the presence of foreign molecules in the body. They can be characterized by their ability to bind both to antigens and to specialized cells or proteins of the immune system. Antibodies are divided into five classes, IgG, IgM, IgA, IgE, and IgD, and are immunoglobulins produced by plasma cells.

As used herein, the term "epitope" is meant to define the region of an antigen that interacts with an antibody. Accordingly, a molecule or other substance, which is an antigen, can include at least one epitope with antibody activity. This can allow for an antigen to have various epitopes recognized by the same or different antibody. Also, an epitope is not an intrinsic property of any particular structure, but can be defined as a binding site that interacts with the antibody.

As used herein, the term "affinity" is meant to refer to a measure of the strength of binding between an epitope and an antibody. Accordingly, a single antibody can have a different affinity for various epitopes. This can allow a single antibody to bind strongly to one epitope and less strongly to another. As such, an antibody can have a first affinity to a drug, such as LEV, and have a second affinity to a LEV derivative. However, it is possible for the antibody to have substantially equivalent or similar affinity for both LEV and a LEV derivative, which allows the analog to be used to generate antibodies for LEV, and their use in competitive binding studies. Thus, LEV derivatives in accordance with the present invention can be used to generate antibodies with affinity for LEV.

As used herein, the term "avidity" is meant to refer to a measure of the overall stability of the complex between antibodies and antigens. The overall stability of an antibody-antigen interaction can be governed by three major factors as follows: (a) the intrinsic affinity of the antibody for the epitope; (b) the valency of the antibody and antigen; and (c) the geometric arrangement of the interacting components. As such, the avidity of the antibody-antigen complex can be modulated by varying the foregoing parameters, as well as others.

As used herein, the term "specificity" is meant to refer to the preferential binding of an antibody with an epitope in comparison with other available epitopes. That is, the specificity of an antibody can preferentially bind LEV and/or analog instead of a LEV metabolite. This can be used to generate anti-LEV antibodies that preferentially bind with LEV over its metabolites so that the true concentration of LEV can be assessed so as to not be contaminated by adverse antibody-metabolite binding. Also, the specificity of an antibody for binding with LEV can be used to tailor analogs with similar or substantially the same specificity as LEV.

As used herein, the term "polyclonal antibody" is meant to refer to a heterogeneous mixture of antibodies with a wide range of specificities and affinities to a given antigen or epitope. Thus, the polyclonal antibody can include a plurality of antibodies, each distinguishable from the others, that bind or otherwise interact with an antigen. The different antibodies that comprise a polyclonal antibody can be produced or generated by injecting an immunogen having an epitope into an animal and, after an appropriate time, collecting and optionally purifying the blood fraction containing the antibodies of interest. In producing antibodies, several parameters can be considered with respect to the final use for the polyclonal antibody. These parameters include the following: (1) the specificity of the antibody (i.e., the ability to distinguish between antigens); (2) the avidity of the antibody (i.e., the strength of binding an epitope); and (3) the titer of the antibody, which determines the optimal dilution of the antibody in the assay system.

As used herein, the term "monoclonal antibody" is meant to refer to an antibody that is isolated from a culture of normal antibody-producing cells and one progenitor cell. A monoclonal antibody can have a homogeneous binding constant, and are well known in the art.

As used herein, "antibody titer" is meant to refer to the reciprocal of the serum dilution. Titers are reported this way for more convenient reporting and formatting. The titer of 1/50000 means that the antibody effectively detects the epitope of an antigen when bound together when the antigen is at a dilution of 1:50000. The titer is calculated by end point titer having about 10% of the maximum O.D.

As used herein, the terms "immunoassay" or "immunodiagnostic" are meant to refer to laboratory techniques that make use of the binding between an antigen and an antibody in order to identify and/or quantify at least one of the specific antigen or specific antibody in a biological sample. Currently, there are three classes of immunoassay, which are described as follows: (1) antibody capture assays; (2) antigen capture assays; and (3) two-antibody sandwich assays. Additionally, it is contemplated that new immunoassays will be developed and will be capable of employing the analogs and antibodies of the present invention.

As used here, the term "competitive immunoassay" is meant to refer to an experimental protocol in which a known amount of an identifiable antigen competes with another antigen for binding with an antibody. That is, a known antigen that binds with a known antibody is combined with a sample that is suspected of containing another antigen that also binds with the known antibody. This allows for the known antigen and another antigen to both compete for the binding site on the antibody. For example, a LEV derivative that binds with an anti-LEV antibody can be combined with a sample suspected of containing LEV, and the analog and LEV compete for binding with the anti-LEV antibody. The competition for binding with the antibody can then be used to determine whether or not LEV is present in the sample, and can further be used to quantify the amount of LEV in the sample.

As used herein, the term "turbidimetric detection" is meant to refer to the measurement of a decrease in the intensity in the transmission, or an increase in absorbance, of incident light due to light scattered by agglutinated particles. A decrease in intensity of transmitted light is measured against a higher starting background intensity of transmitted light. Usually, the reading is made with a detector in line with the light source, wherein the agglutination of particles inhibits transmission of the light. Therefore, the inhibition or promotion of agglutination can be used as a means for assessing the presence of a target analyte, such as LEV. Turbidimetric assays may be easily adapted to a variety of clinical analyzers.

As used herein, the term "microparticle agglutination assays" is meant to refer to immunoassays that use the principle of inhibiting agglutination of microparticles by a target analyte. That is, decreased agglutination is attributed to the presence of the target analyte. For example, a derivative of the target drug is covalently linked to the surface of microparticle and/or the sensitized particles are agglutinated by a monoclonal antibody. When a sample contains free drug the agglutination is inhibited in proportion to the drug concentration, which leads to a classic inhibition curve relating drug concentration to absorbance.

As used herein, the term "operative group" is meant to refer to a molecule or macromolecule coupled to LEV through a linker group. An operative group can include an immunogenic moiety, antigen moiety, tracer moiety, and the like. Additionally, the Z group in the chemical scaffolds described herein is an operative group. As such, the operative group can be coupled to the Y linker group and provide an additional functionality to the LEV derivative.

As used herein, the terms "active ester" or "activated ester" are meant to refer to an ester group that can react with a free amino group of a compound such as, for example, peptides and proteins. An active ester can include a carboxyl group linked to an active leaving group. Often, the active leaving group includes the ester oxygen so the active leaving group removes the ester oxygen. For example, an active ester is susceptible to being displaced by a primary amine, which results in the removal of the ester oxygen and formation of an amide group. Examples of active leaving groups that form active esters include N-hydroxysuccinimide ("NHS"), p-nitrophenyl, pentafluorophenyl, N-hydroxybenzotriazolyl, and the like. Accordingly, use of the term "NHS" is meant to be defined as N-hydroxysuccinimide.

As used herein, the terms "label," "detector molecule," or "tracer" are meant to refer to any operative group which produces, or can be induced to produce, a detectable signal. The label can be conjugated to LEV, LEV derivative synthesis starting materials and/or intermediates, LEV derivative, hapten, analyte, immunogen, antibody, or to another molecule such as a receptor or a molecule that can bind to a receptor. Non-limiting examples of tracers include radioactive isotopes, enzymes, enzyme fragments, enzyme substrates, enzyme inhibitors, coenzymes, catalysts, fluorophores, dyes, chemiluminescers, luminescers, sensitizers, non-magnetic or magnetic particles, solid supports, liposomes, ligands, receptors, hapten radioactive isotopes, and the like. As described herein, for example, the LEV derivative synthesis starting materials and/or synthesis intermediates can be coupled to a variety of tracer moieties (e.g., fluorophores) that can be used to track starting materials and product in synthesis reactions. As also described herein, LEV derivatives can be coupled to a variety of labels by methods well known in the art to provide a variety of reagents useful in various immunoassay formats. For detecting the results of the immunoassays, detector molecules such as fluorophores, for example, fluorescein, radiolabels, or chemiluminescent groups can be coupled to the analogs to produce tracers.

As used herein, the terms "linking group" or "linker" are meant to refer to a portion of a chemical structure that connects two or more substructures such as LEV, LEV derivatives, haptens, and operative groups, such as immunogenic moieties, carriers, immunogens, labels, tracers, and the like. A linking group can have at least one uninterrupted chain of atoms other than hydrogen (or other monovalent atoms) extending between the substructures. Usually, a linking group includes a chain of carbon atoms or hetero atoms, which can be substituted or unsubstituted. The atoms of a linking group and the atoms of a chain within a linking group can be interconnected by chemical bonds. For example, linkers maybe straight or branched, substituted or unsubstituted, saturated or unsaturated chains, wherein the chain atoms can include carbon and/or hetero atoms. This can include one or more hetero atoms within the chain or at termini of the chains. Additionally, a linking group may also include cyclic and/or aromatic groups as part of the chain or as a substitution on one of the atoms in the chain. The number of atoms in a linking group or linker is determined by counting the atoms other than hydrogen in the backbone of the chain, which is the shortest route between the substructures being connected. Linking groups may be used to provide an available site on a hapten for conjugating a hapten with a tracer, label, carrier, immunogenic moiety, and the like.

As used herein, the term "hetero atoms" is meant to refer to atoms other than carbon atoms such as oxygen, nitrogen, sulfur, phosphorus, and the like. Usually, a heteroatom is multivalent so as to form at least two covalent bonds, which can be used in a linking group or other moiety.

As used herein, the term "biological sample" is meant to refer to a solid or fluid sample that is obtained from a biological entity. As such, a biological sample can include, but is not limited to, any quantity of a substance from a living thing or formerly living thing, such as humans and other animals.

Such a substance can include, but is not limited to, blood, serum, plasma, urine, tears, cells, organs, tissues, bone, bone marrow, lymph, lymph nodes, synovial tissue, chondrocytes, synovial macrophages, endothelial cells, skin, and the like.

As used herein, the term "patient" is meant to refer to human and other animal subjects. More particularly, a patient is a human or other animal subject needing an anti-epileptic drug such as LEV.

The LEV derivatives can include a LEV molecule coupled to a linker moiety, and optionally include an operative group. The linker moiety and operative group can be any of a wide range of chemical compounds that can modify the physico-chemical properties of LEV. Accordingly, the linker moiety can be comprised of an alkyl, aliphatic, straight chain aliphatic, branched aliphatic, substituted aliphatic, cyclic aliphatic, heterocyclic aliphatic, aromatic, heteroaromatic, polyaromatic, and the like.

As used herein, the term "aliphatic" is meant to refer to a hydrocarbyl moiety, such as an alkyl group, that can be straight or branched, saturated or unsaturated, and/or substituted or unsubstituted, which has twenty or less carbons or hetero atoms in the backbone. Additionally, an aliphatic can include 10 or less carbons or hetero atoms in the backbone. An aliphatic group may comprise moieties that are linear, branched, cyclic and/or heterocyclic, and contain functional groups such as ethers, ketones, aldehydes, carboxylates, and the like. Exemplary aliphatic groups include but are not limited to substituted and/or unsubstituted groups of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, alkyl groups of higher number of carbons and the like, as well as 2-methyl-propyl, 2-methyl-4-ethylbutyl, 2,4-diethylpropyl, 3-propyl-butyl, 2,8-dibutyldecyl, 6,6-dimethyloctyl, 6-propyl-6-butyloctyl, 2-methylbutyl, 2-methylpentyl, 3-methylpentyl, 2-ethylhexyl, and the like. The terms aliphatic or alkyl also encompasses alkenyl groups, such as vinyl, allyl, aralkyl and alkynyl groups.

Substitutions within an aliphatic group can include any atom or group that can be tolerated in the aliphatic moiety, including but not limited to halogens, sulfurs, thiols, thioethers, thioesters, amines (primary, secondary, or tertiary), amides, ethers, esters, alcohols, oxygen, and the like. The aliphatic groups can by way of example also comprise modifications such as azo groups, keto groups, aldehyde groups, carbonyl groups, carboxyl groups, nitro, nitroso or nitrile groups, heterocycles such as imidazole, hydrazino or hydroxylamino groups, isocyanate or cyanate groups, and sulfur containing groups such as sulfoxide, sulfone, sulfide, and disulfide. Additionally, the substitutions can be via single, double, or triple bonds, when relevant or possible.

Further, aliphatic groups may also contain hetero substitutions, which are substitutions of carbon atoms, by hetero atoms such as, for example, nitrogen, oxygen, phosphorous, or sulfur. As such, a linker comprised of a substituted aliphatic can have a backbone comprised of carbon, nitrogen, oxygen, sulfur, phosphorous, and/or the like. Heterocyclic substitutions refer to alkyl rings having one or more hetero atoms. Examples of heterocyclic moieties include but are not limited to morpholino, imidazole, and pyrrolidino.

As used herein, the term "aromatic" is meant to refer to molecule is one in which electrons are free to cycle around circular or cyclic arrangements of atoms, which are alternately singly and doubly bonded to one another. More properly, these bonds may be seen as a hybrid of a single bond and a double bond, each bond in the ring being identical to every other.

As used herein, the term "amine" is meant to refer to moieties that can be derived directly or indirectly from ammonia by replacing one, two, or three hydrogen atoms by other groups, such as, for example, alkyl groups. Primary amines have the general structures $RNH_2$ and secondary amines have the general structure $R_2NH$. The term amine includes, but is not limited to methylamine, ethylamine, propylamine, isopropylamine, aniline, cyclohexylamine, benzylamine, polycyclic amines, heteroatom substituted aryl and alkylamines, dimethylamine, diethylamine, diisopropylamine, dibutylamine, methylpropylamine, methylhexylamine, methylcyclopropylamine, ethylcyclohexylamine, methylbenzylamine, methycyclohexylmethylamine, butylcyclohexylamine, morpholine, thiomorpholine, pyrrolidine, piperidine, 2,6-dimethylpiperidine, piperazine, and heteroatom substituted alkyl or aryl secondary amines.

As used herein, the term "poly(amino acid)" or "polypeptide" is a polyamide formed from amino acids. Poly(amino acid)s will generally range from about 200-2,000 molecular weight or greater than about 2,000 molecular weight, or having no upper molecular weight limit, and normally being less than 10,000,000 and usually not more than about 600,000 daltons. There will usually be different ranges, depending on whether an immunogenic carrier or an enzyme is involved.

As used herein, the term "peptide" is meant to refer to any compound formed by the linkage of two or more amino acids by amide (peptide) bonds, usually a polymer of α-amino acids in which α-amino group of each amino acid residue (except the $NH_2$ terminus) is linked to the α-carboxyl group of the next residue in a linear chain. The terms "peptide," "polypeptide," and "poly(amino acid)" are used synonymously herein to refer to this class of compounds without restriction as to size. The largest members of this class are referred to as proteins having a defined polypeptide sequence.

Additionally, the terms used herein to describe the invention can be construed using the foregoing definitions and/or definitions well known in the art. As such, the foregoing terminology is meant to describe the invention and is not intended to be limiting.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A chemical composition, comprising a levetiracetam ("LEV") derivative of Formula 2:

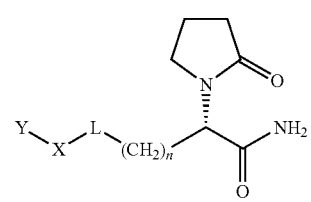

Formula 2 wherein Y is $Y_1$—Z, and wherein n, L, X, and $Y_1$—Z of Formula 2 are selected from the group consisting of:

n=4, L=NHCO, X=Ph, and Y$_1$—Z=CO—NHS;
n=4, L=NHCO, X=Ph, and Y$_1$—Z=CO—KLH; and
n=4, L=NHCO, X=Ph, and Y$_1$—Z=CO—BSA;

2. A kit for use in an immunodiagnostic assay for detecting the presence of LEV in a sample, the kit comprising:
a LEV derivative having a chemical structure of Formula 2;

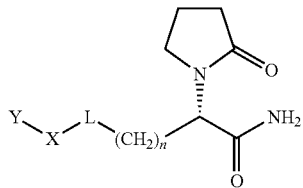

Formula 2 wherein Y is Y$_1$—Z, and wherein n, L, X, and Y$_1$—Z of Formula 2 are selected from the group consisting of:

n=4, L=NHCO, X=Ph, and Y$_1$—Z=CO—NHS;
n=4, L=NHCO, X=Ph, and Y$_1$—Z=CO—KLH; and
n=4, L=NHCO, X=Ph, and Y$_1$—Z=CO—BSA.

3. The kit of claim 2, wherein the LEV derivative is coupled with one of a particle, magnetic particle, microparticle, microsphere, support, enzyme donor, or enzyme acceptor.

4. The kit of claim 2, further comprising at least one of the following:
   a stock composition of LEV;
   a series of compositions containing LEV at different concentrations, the series of compositions forming a concentration gradient;
   the LEV derivative having a tracer conjugate;
   the LEV derivative coupled to a microparticle;
   the LEV derivative having an enzyme donor, and a corresponding enzyme or;
   the LEV derivative having an enzyme acceptor, and a corresponding enzyme donor.

* * * * *